(12) United States Patent
Vela Hernández et al.

(10) Patent No.: US 9,844,516 B2
(45) Date of Patent: Dec. 19, 2017

(54) SIGMA LIGANDS FOR USE IN THE PREVENTION AND/OR TREATMENT OF POST-OPERATIVE PAIN

(75) Inventors: José Miguel Vela Hernández, Barcelona (ES); Daniel Zamanillo-Castanedo, Barcelona (ES); Margarita Puig Riera de Conias, Barcelona (ES)

(73) Assignee: Laboratorios De Dr. Esteve, Barcelona (ES)

( * ) Notice: Subject to any disclaimer, the term of this patent is extended or adjusted under 35 U.S.C. 154(b) by 0 days.

(21) Appl. No.: 13/574,940

(22) PCT Filed: Feb. 4, 2011

(86) PCT No.: PCT/EP2011/051643
§ 371 (c)(1),
(2), (4) Date: Jul. 24, 2012

(87) PCT Pub. No.: WO2011/095584
PCT Pub. Date: Aug. 11, 2011

(65) Prior Publication Data
US 2012/0302568 A1 Nov. 29, 2012

(30) Foreign Application Priority Data
Feb. 4, 2010 (EP) .................... 10382024

(51) Int. Cl.
*A61K 31/415* (2006.01)
*A61K 31/00* (2006.01)
*A61K 31/416* (2006.01)
*A61K 31/4196* (2006.01)
*A61K 31/5377* (2006.01)

(52) U.S. Cl.
CPC ............ *A61K 31/00* (2013.01); *A61K 31/415* (2013.01); *A61K 31/416* (2013.01); *A61K 31/4196* (2013.01); *A61K 31/5377* (2013.01)

(58) Field of Classification Search
CPC .......................... A61K 31/415; A61K 31/416
See application file for complete search history.

(56) References Cited

FOREIGN PATENT DOCUMENTS

| | | |
|---|---|---|
| EP | 0248594 A2 | 12/1987 |
| EP | 0414289 A1 | 2/1991 |
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 B1 | 5/1994 |
| EP | 0975648 A1 | 2/2000 |
| EP | 1130018 A1 | 9/2001 |
| EP | 1634872 A1 | 3/2006 |
| EP | 1634873 A1 | 3/2006 |
| EP | 1 787 679 A1 | 5/2007 |
| EP | 1829866 A1 | 9/2007 |
| EP | 1829875 A1 | 9/2007 |
| EP | 1847542 A1 | 10/2007 |
| EP | 2090311 A1 | 8/2009 |
| EP | 2112139 A1 | 10/2009 |
| EP | 2 116 539 A1 | 11/2009 |
| EP | 2113501 A1 | 11/2009 |
| EP | 2353598 | 8/2010 |
| EP | 2254579 A1 | 12/2010 |
| EP | 2992236 | 3/2011 |
| EP | 2353591 A1 | 8/2011 |
| EP | 2361904 A1 | 8/2011 |
| EP | 2415471 A1 | 2/2012 |
| EP | 2335688 A1 | 6/2012 |
| EP | 2460519 A1 | 6/2012 |
| EP | 2460804 A1 | 6/2012 |
| EP | 2524694 A1 | 11/2012 |
| EP | 2395003 A1 | 12/2012 |
| EP | 2426111 A1 | 3/2013 |
| EP | 2426112 A1 | 3/2013 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 A | 10/1967 |
| GB | 1496411 A | 12/1977 |
| GB | 2026482 A | 7/1987 |
| IL | 151533 B | 3/2008 |

(Continued)

OTHER PUBLICATIONS

Kawamata et al 'Experimental incision-induced pain in human skin: effects of systemic lidocaine on flare formation and hyperalgesia' Pain, vol. 100, p. 77-89, 2002.*
Brennan, T.J. et al., "Characterization of a rat model of incisional pain", Pain, 1996, vol. 64, pp. 493-501.
Hellwell, S.B. and Bowen, W.D. "A sigma-like binding site in rat pheochromocytoma (PC12) cells: decreased affinity for (+)-benzomorphans and lower molecular weight suggest a different sigma receptor form from that of guinea pig brain", Brain Research, 1990, vol. 527, pp. 244-253.
Leitner, M.L. et al., "Regional variation in the ratio of $\sigma_1$ or $\sigma_2$ binding in rat brain", European Journal of Pharmacology, 1994, vol. 259, pp. 65-69.

(Continued)

*Primary Examiner* — Craig Ricci
*Assistant Examiner* — Christopher R Stone
(74) *Attorney, Agent, or Firm* — Gary J. Gershik; Cooper & Dunham LLP

(57) ABSTRACT

The invention refers to the use of a sigma ligand, particularly a sigma ligand of formulae (I), (II) or (III) to prevent and/or treat acute and chronic pain developed as a consequence of surgery, especially superficial and/or deep pain secondary to surgical tissue injury, and peripheral neuropathic pain, neuralgia, allodynia, causalgia, hyperalgesia, hyperesthesia, hyperpathia, neuritis or neuropathy secondary to surgical procedure.

10 Claims, 6 Drawing Sheets

(56) References Cited

FOREIGN PATENT DOCUMENTS

| | | |
|---|---|---|
| JP | 1992/364129 | 12/1992 |
| JP | 10036259 | 2/1998 |
| JP | 10055048 | 2/1998 |
| JP | 2004/196678 | 7/2004 |
| JP | 2008/510767 | 4/2008 |
| JP | 2008/179541 | 8/2008 |
| RU | 2218187 C2 | 10/2003 |
| RU | 2322977 C1 | 4/2008 |
| RU | 2382646 C1 | 2/2010 |
| SU | 11248 | 9/1929 |
| WO | WO-1991/09594 A1 | 7/1991 |
| WO | WO-1992/09560 A1 | 6/1992 |
| WO | WO-1993/23383 A1 | 12/1992 |
| WO | WO-1996/016063 A1 | 5/1996 |
| WO | WO-1998/046618 A1 | 10/1998 |
| WO | WO-1999/01444 A1 | 1/1999 |
| WO | WO-1999/21824 A1 | 5/1999 |
| WO | WO-1999/31074 A2 | 6/1999 |
| WO | WO-1999/31075 A1 | 6/1999 |
| WO | WO-1999/059409 A1 | 11/1999 |
| WO | WO-1999/61424 A1 | 12/1999 |
| WO | WO-2000/31020 A1 | 2/2000 |
| WO | WO-2000/20005 A1 | 4/2000 |
| WO | WO-2000/27394 A1 | 5/2000 |
| WO | WO-2000/40275 A2 | 7/2000 |
| WO | WO-2000/73259 A1 | 12/2000 |
| WO | WO-2000/73300 A1 | 12/2000 |
| WO | WO-2002/085839 A1 | 10/2002 |
| WO | WO-2002/092573 A2 | 11/2002 |
| WO | WO-2002/102387 A1 | 12/2002 |
| WO | WO-2003/080183 A1 | 10/2003 |
| WO | WO-2004/016592 A1 | 2/2004 |
| WO | WO-2004/017961 A2 | 3/2004 |
| WO | WO-2004/046129 A2 | 6/2004 |
| WO | WO-2005/061462 A2 | 7/2005 |
| WO | WO-2006/010587 A1 | 2/2006 |
| WO | WO 2006/021462 A1 | 3/2006 |
| WO | WO 2006/021463 A1 | 3/2006 |
| WO | WO-2006/027221 A1 | 3/2006 |
| WO | WO-2007/002559 A1 | 1/2007 |
| WO | WO-2007/025613 A2 | 3/2007 |
| WO | WO-2007/046550 A1 | 4/2007 |
| WO | WO-2007/079086 A1 | 7/2007 |
| WO | WO-2007/090661 A2 | 8/2007 |
| WO | WO-2007-098939 A1 | 9/2007 |
| WO | WO-2007/098963 A1 | 9/2007 |
| WO | WO-2007/098964 A2 | 9/2007 |
| WO | WO-2007/108517 A1 | 9/2007 |
| WO | WO-2007/110221 A1 | 10/2007 |
| WO | WO-2007/141018 A1 | 12/2007 |
| WO | WO 2008/015266 A1 | 2/2008 |
| WO | WO 2008/055932 A1 | 5/2008 |
| WO | WO-2008/108517 A2 | 9/2008 |
| WO | WO 2008/149062 | 12/2008 |
| WO | WO-2009/038112 A1 | 3/2009 |
| WO | WO-2009/071657 A1 | 6/2009 |
| WO | WO 2009/103487 A1 | 8/2009 |
| WO | WO 2009/130310 A1 | 10/2009 |
| WO | WO-2011/095579 A1 | 1/2011 |
| WO | WO 2011/018487 A1 | 2/2011 |
| WO | WO 2011/064296 A1 | 6/2011 |
| WO | WO-2011/064296 A1 | 6/2011 |
| WO | WO-2011/064315 A1 | 6/2011 |
| WO | WO-2011/095584 A1 | 8/2011 |
| WO | WO-2011/095585 A1 | 8/2011 |
| WO | WO-2011/144721 A1 | 11/2011 |
| WO | WO-2011/147910 A1 | 12/2011 |
| WO | WO-2012/016980 A1 | 2/2012 |
| WO | WO-2012/019984 A1 | 2/2012 |
| WO | WO-1999/31057 A1 | 6/2012 |
| WO | WO-2012/072781 A1 | 6/2012 |
| WO | WO-2012/072782 A1 | 6/2012 |
| WO | WO-2012/156497 A1 | 11/2012 |
| WO | WO-2012/158413 A2 | 11/2012 |
| WO | WO-2014/170319 A1 | 10/2014 |
| WO | WO-2014-207024 A1 | 12/2014 |
| WO | WO 2015/036470 A1 | 3/2015 |
| WO | WO-2015-091505 A1 | 6/2015 |
| WO | WO-2015/091508 A1 | 6/2015 |

OTHER PUBLICATIONS

Mersky, H. and Bogduk, N., IASP Classification of Chronic Pain, 2002, $2^{nd}$ edition, pp. 210-213.

Prasad, P.D. et al., "Exon-Intron Structure, Analysis of Promoter Region, and Chromosomal Localization of the Human Type 1 σ Receptor Gene", Journal of Neurochemistry, 1998, vol. 70, No. 2, pp. 443-451.

Quirion, R. et al., "A proposal for the classification of sigma binding sites", Trends in Pharmacological Science, 1992, vol. 13, pp. 84-86.

Ronsisvalle, G. et al., "Opioid and sigma receptor studies. New developments in the design of selective sigma ligands", Pure and Applied Chemistry, 2001, vol. 73, No. 9, pp. 1499-1509.

Zahn, P.K. et al., "Mechanisms for Pain Caused by Incisions", Regional Anesthesia and Pain Medicine, 2002, vol. 27, No. 5, pp. 514-516.

International Search Report issued by the International Searching Authority (ISA/O.E.P.M.) on Mar. 9, 2011 in connection with International Application No. PCT/EP2011/051643.

Finnerup, N. B., Sindrup, S.H., Jensen, T.S. The evidence fear pharmacological treatment of neuropathic pain. Pain 2010; 150:573-581.

Kehlet, H., Dahl, J.B. Anaesthesia, surgery, and challenges in postoperative recovery. Lancet 2003; 362:1921-28.

Kehlet, H., Jensen, T.S., Woolf, C.J. Persistent postsurgical pain: risk factors and prevention. Lancet 2006; 367:1618-25.

Kehilet, H., Wilkinson, R.C., Fischer, H.B.J., Camu, F. PROSPECT: evidence-based, procedure-specific postoperative pain, management. Best Practice Res Clin Anaesthesiol. 2007; 21:149-159.

Saha, M., Skopelja, S., Martínez, E., Alvarez, D.L., Liponis, B.S., Romero-Sandoval, E.A. Spinal Mitogen-Activated Protein Kinase Phosphatase-3 (MKP-3) is necessary for the normal resolution of mechanical allodynia in a mouse model of acute postoperative pain. J. Neurosci. 2013; 43:17182-7.

Whittington, C.M., Koh, J.M.S., Warren, W.C., Papenfuss A.T., Torres, A.M., Kuchel, P.W., Belov, K. Understanding and utilising mammalian venom via a platypus venom transcriptome. J. Proteomics 2009; 72;155-164.

Yasuda, M., Kido, K., Ohtani, N., Masaki, E. Mast cell stabilization promotes antinociceptive effects in a mouse model of postoperative pain. J. Pain Res. 2013; 6:161-166.

PCT International Publication No. WO 2006/118307 Al (Mochida Pharmaceutical Co., Ltd.) Nov. 9, 2006.

PCT International Publication No. WO 2007/098953 A1 (Laboratorios Del Dr. Esteve, S.A.) Sep. 7, 2007.

Russian patent No. RU 2 322 977 C1 (Vladimirovich et al.) Aug. 1, 2006, including English Translation.

Cepeda, MS, "Comparison of Morphine, ketorolac, and their combination for postoperative pain: results form a large, randomized, double-blind trial", Anethesiology, 2005, vol. 103, No. 6, pp. 1225-1232.

Gabriel, AF, Preoperative housing in an enriched environment significantly reduces the duration of post-operative pain in a rat model of knee inflammation, Neurosci. Lett. 2010, vol. 469, No. 2, pp. 219 232.

Chen, S.R. et al., "Synergistic Effect between Intrathecal Non-NMDA Antagonist and Gabapentin on Allodynia Induced by Spinal Nerve Ligation in Rats", Anesthesiology, 2000, vol. 92, pp. 500-506.

Du, J. et al., "Kainate-induced Excitation and Sensitization of Nociceptors in Normal and Inflamed Rat Glabrous Skin", Neuroscience, 2006, vol. 137, pp. 999-1013.

Levine, J.D. et al., "Desiperamide Enhances Opiate Postoperative Analgesia" Pain, 1986, vol. 27, pp. 45-49.

(56) References Cited

OTHER PUBLICATIONS

Max M.B., "Endogenous Monoamine Analgesic Systems: Amitriptyline in Painful Diabetic Neuropathy", Anesth Prog, 1987, vol. 34, pp. 113-127.
Laggner, C. al., "Discovery of High-Affinity Ligands of σ Receptor, ZPG2, and Emopamil Binding Protein by Pharmacophore Modeling and Virtual Screening," J. Med. Chem. 2005, 48:4754-4764
Glass PSA, Camporesi EM, Shafron. D, Quill T, Reves JG. Evaluation of Pentamorphone in Humans: A New Potent Opiate. Anesth Analg. 1989;68:302-7.
Wong HY, Parker RK, Fragen R, White PF. Pentamorphone for Management of Postoperative Pain. Anesth Analg. 1991;72:656-60.
O'Neill J, Brock C, Olesen AE, Andresen T, Nilsson M, Dickenson AH. Unravelling the rnystery of capsaicin: a tool to understand and treat pain. Pharrnacol Rev. Oct. 2012;64(4):939-71.
Sakurada T, Matsumura T, Moriyarna T, Sakurada C, Ueno S, Sakurada S. Differential effects of intraplantar capsazepine and ruthenium red on capsaicin-induced desensitization in mice. Pharmacol Biochern Behav. Apr. 2003;75(1):1 15-21.
"Chemotherapy at home, pain and its treatment", Soins, Table Ronde, Office De Publicite Generale, Paris, FR, (Sep. 1, 1989), No. 528, ISSN 0038-0814, pp. 17-20, XP009107313 [A] 1-16. * p. 19 *.
Aapro et al., "Anticipatory nausea and vomiting," Support Care Cancer, 2005, 13: 117-121.
Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.
Abbott, C, A., et al., "The North-West Diabetes Foot Care Study: incidence of, and risk factors for, new diabetic foot ulceration in a community-based patient cohort", Diabetic Medicine, vol. 19, 2002, pp. 377-384.
Abraham, D.J., et al., "Burger's Medicinal Chemistry: Drug Discovery and Development" 7th edition, 8 volume set, 2010.
Abrams, P., et al., "The standardisation of terminology of lower urinary tract function: report from the standardisation sub-committee of the International Continence Society", Neurology and Urodynamics, 21, 2002, pp. 167-178.
Acta Obstetrica Gynecologica Japonica, 2000, vol. 52 (6), pp. 117-120.
Advokat, C., et al., "Selective antinociceptive effect of excitatory amino acid antagonists in intact and acute spinal rats," Pharmacology Biochemistry and Behaviour 51(4):855-860 1995.
Alberts, D.S., et al., "Cisplatin-associated neurotoxicity: can it be prevented?" Anti-cancer Drugs, 1995, vol. 6, pp. 369-383.
Almerico, AM., "1-Methyi-3H-pyrazolo[1, 2-a]benzo[1, 2, 3, 4] 1 tetrazin-3-ones: Design, synthesis and biological activity of new antitumor agents", Journal of Medicinal Chemistry, vol. 48, 2005, pp. 2859-2866.
Anderson, B. D. et al., "Preparation of Water-Soluble Compounds Through Salt Formation" The Practice of Medicinal Chemistry, Chapter 34, pp. 739-754 (1996).
Angst, M.S., et al., "Opioid-induced Hyperalgesia: A Qualitative Systematic Review," Anesthesiology. vol. 104 pp. 570-587 (2006).
Anonymous "Opioid-Induced hyperalgesia," http://lweb.archive.org/web/20080712205531/http://en.wikipedia.org/wiki/Opioid-inducedhyperalgesia (retrieved Feb. 16, 2017).
Anton, E., "Delayed toxicity of cyclophosphamide on the bladder of DBA/2 and C57BL/6 female mouse," Int. J. Exp. Path., 83, 2002, pp. 47-53.
Arafa, et. al., Journal of Medicinal Chemistry, 2005, American Chemical Society, vol. 48, pp. 5480-5488.
Argyriou et al., "Bortezomib-induced peripheral neuropathy in multiple myeloma: a comprehensive review of the literature," Blood, 2008, 112(5): 1593-1599.
Arthritis [online], [retrieved on Nov. 20, 2007]. Retrieved from the Internet, URL; http://www.nlm.nih.gov/medlineplus/ency/article/001243.htm>.

Asano, T., et al. Antinociception by epidural and systemic alpha(2)adrenoceptor agonists and their binding affinity in rat spinal cord and brain, Anesth Anal g. 2000; 90 (2): 400-407.
Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.
Barnes et al., "Reserpine, Para-Cholorophenylalanine and Fenfluramine Antagonise Cisplatin-Induced Emesis in the Ferret," Neuropharmacology, 1988, 27(8): 783-790.
Batson, et al., "a-Hydroxy Cyclopentenones from a-Diketones", Organic Letters, vol. 7, No. 13, pp. 2771-2774, 2005.
Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.
Bennett, G. J. "Pathophysiology and Animal Models of Cancer-Related Painful Peripheral Neuropathy", The Oncologist, 2010, 15 (suppl2), pp. 9-12.
Berge et al. "Pharmaceutical Salts," Journal of Pharmaceutical Sciences, 1977, 66(1): 1-19.
Bon, K., et al., "Characterization of cyclophosphamide cystitis, a model of visceral and referred pain, in the mouse: species and strain differences.", J UROL., (2003), vol. 170, No. 3, pp. 1008-1012.
Botting, R.M.; Clinical Infectious Diseases, 2000, 31, S202-10.
Boulton, A.J.M., et al., "Diabetic Neuropathies" Diabetes Care, vol. 28, No. 4, Apr. 2005, pp. 956-962.
Brammer et al., "Interactions between 3,4-methlenedioxymethamphetamine and σ1 receptors," European Journal of Pharmacology, 2006, 553: 141-145.
Cobos, E. J., et al., Pharmacology and therapeutic potential of Sigma(1) receptor ligands. Curr. Neuropharmacol. 2008; 6, 344-366.
Brussee, et al., Diabetes, 2008, 57: 1664-1673, "Distal Degenerative Sensory Neuropathy in a Long-Term Type 2 Diabetes Rat Model".
Kautio, et al., "Amitriptyline in the Prevention of Chemotherapy-induced Neuropathic Symptoms" (2009) Anticancer Research, 29:2601-2606.
Kautio, et al., "Amitriptyline in the Treatment of Chemotherapy-Induced Neuropathic Symptoms" (2008) Journal of Pain and Symptom Management, 35(1):31-39.
Bryant et al., Opioids and addiction: Emerging pharmaceutical strategies for reducing reward and opponent processes, Clinical Neuroscience Research, 2005, 5, pp. 103-115.
Buerkle, H., Yaksh, T. L. Pharmacological evidence for different alpha 2-adrenergic receptor sites mediating analgesia and sedation in the rat, Br J Anaesth. 1998; 81 (2): 208-215.
Bura, S.A. et al., "Evaluation of The Effect of the Selective Sigma-1 Receptor Antagonist S1RA in Neuropathic Pain Using an Operant Model", Eur J. Pain Supplements 2010, vol. 4, p. 49 (Abstract Only).
Buvanendran, A., et al. "Characterization of a New Animal Model for Evaluation of Persistent Postthoracotomy Pain", Anesth Analg, 2004, vol. 99, pp. 1453-1460.
Cancer [online], [retrieved on Jul. 6, 2007]. Retrieved from the Internet, URL; http://www.nim.nih.gov/medlineplus/cancer.html>.
Lala et al., "Role of Nitric Oxide in Tumor Progression: Lessons from Experimental Tumors," Cancer and Metastasis Reviews, 17(1), 91-106, 1998.
Cao, J., et al., "Dual Probes for the Dopamine Transporter and sigmal Receptors: Novel Piperazinyl Alkyl-bis(4-fluorophenyl)amine Analogues as Potential Cocaine-Abuse Therapeutic Agents", J. Med. Chem, 2003, pp. 2589-2598.
Carlsson, et al., "Interaction of pentobarbital and morphine in the tail-flick test performed on rates: synergism at the spinal and antagonism at the supraspinal level", NeuroSci. Lett.; 1986; 71; pp. 356-360.
Carrle, et al., Int Orthopaedics vol. 30, pase 445-451. publication year: 2006.

(56) References Cited

OTHER PUBLICATIONS

Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans—Smart Nurse, Nov. 2007, vol. 9, No. 11, pp. 1238-1239.
Celerier, et al., "Progressive Enhancement of Delayed Hyperalgesia Induced by Repeated Heroin Administration: A Sensitization Process," The Journal of Neuroscience. vol. 21, No. 11 pp. 4074-4080 (2001).
Davies, A., et al., "Functional biology of the alpha-2-delta subunits of voltage-gated calcium channels," trends in Pharmacological Sciences, vol. 28, No. 5, 2007, pp. 220-228.
Cersosimo, R.J., "Oxaliplatin-Associated Neuropathy: A Review", The Annals of Pharmacotherapy, 2005 vol. 39 pp. 128-135.
Chaplan S. R., et al., "Quantitative assessment of tactile allodynia in the rat paw", J. Neurosci. Methods, (1994), vol. 53, pp. 55-63.
Chaudhry, V., et al., "Bortezomib and thalidomide-induced subacute demyelinating polyneuropathy," Clinical Neurophysiology, 2009, vol. 120, p. e111.
Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.
Cheng, et al., Modern Bone Science, Modern Orthopaedics, "14.2.2 Drug Analgesia," p. 164, 2010, including English translation.
Maurice, T., Su, T. P., The pharmacology of Sigma-1receptors. Pharmacal. Ther. 2009; 124, 195-206.
Chen, D., et al., "Development and application of rodent models for type 2 Diabetes", Diabetes, Obesity and Metabolism, vol. 7, 2005, pp. 307-317.
Cherny, N., "Opioids and The Management of Cancer Pain", Eur. J. Cancer Supplement 2005, vol. 3, pp. 61-75.
Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61.
Chien, C., et al., "Sigma antagonists potentiate opioid analgesia in rats," Neuroscience Letters, vol. 190, No. 2, 1995, pp. 137-139.
Chien, et al., "Selective Antagonism of Opioid Analgesia by a Sigma System," J. Pharmacol. Exp. Ther.; 1994; 271; pp. 1583-1590.
Cited ref STN search abstract JP10055048. p. 8.
Clark, J.B., et al., "The Diabetic Zucker Fatty Rat (41611)", Proceedings of the society for experimental Biology and Medicine, 1983, vol. 173, pp. 68-75.
Consilium MedSigma-receptors: new potentials of the treatment of depressions. Consilium Medicumicum 2012, vol. 14, No. 2 (found in the Internet: URL<new.Consiliummedicum.com/magazine/cm/medicum/article/21505, paragraphs 4-8).
Final Office Action dated Nov. 29, 2007 in related priority application U.S. Appl. No. 10/978,250.
Final Office Action dated Oct. 20, 2008 in related priority application U.S. Appl. No. 10/978,250.
Non-Final Office Action dated Apr. 16, 2008 in related priority application U.S. Appl. No. 10/978,250.
Non-Final Office Action dated Jun. 14, 2007 in related priority application U.S. Appl. No. 10/978,250.
Requirement for Restriction/Election dated Apr. 5, 2007 in related priority application U.S. Appl. No. 10/978,250.
Coxon, et al., "Acid-catalysed Rearrangements of trans- and cis-1-Acetoxy-3,4-epoxypentane and 1-Acetoxy-4,5- epoxyhexane", J. Chem. Soc. Chem. Commun., 8, pp. 261-262, 1973.
Crawford et al., "Sigma-2 Receptor Agonists Activate a Novel Apoptotic Pathway and Potentiate Antineoplastic Drugs in Breast Tumor Cell Lines," Cancer Research, 2002, 62: 313-322.
D'Amour, F. E. and Smith, D. L. A method for determining the loss of pain sensation, J. Pharmacal. Exp. Ther. 1941; 72:74-79.

Dani, et al. (2007) The local antinociceptive effects of paracetamol in neuropathic pain are mediated by cannabinoid receptors. European Journal of Pharmacology 573(1-3): 214-215.
Danziger, et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.
Daousi, C., et al., "Chronic painful peripheral neuropathy in an urban community: a controlled comparison of people with and without diabetes", Diabetic Medicine, vol. 21, 2004, pp. 976-982.
Dapeng Ll "The Role of Glial Cells in . . . Pain", Thesis of Huazhong, University of Science and Technology, 2006, p. 24; Publication Date: Feb. 19, 2008.
Database WPI Week 200451 Thomson Scientific, London, GB; An 2004-529624-& JP 2004 196678 A (Dainippon Pharm Co Ltd) Jul. 15, 2004.
Dauben, W., et al., "Organic Reactions at High Pressure Preparation of Wittig Phosphonium Salts at Ambient Temperature", J. Org. Chem., 1984, vol. 49, pp. 4293-4295.
Epstein, et al., "Oral topical doxepin rinse: analgesic effect in patients with oral mucosal pain due to cancer or cancer therapy" (2001) Oral Oncology, 37:632-637.
DeHaven-Hudkins, et al., "Characterization of the binding of [H] (+)-pentazocine to σ recognition sites in guinea pig brain," European Journal of Pharmacology—Molecular Pharmacology Section, 1992, vol. 227, pp. 371-378.
Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9. * the whole document *.
Dewar, M. J. S., "Attempts to find new Antimalarials. Part XXI", Journal of the Chemical Society, (1944), pp. 615-619.
Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.
Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.
Dixon W.J. "Efficient Analysis of Experimental Observations," Ann. Rev. Pharmacol. Toxicol, 1990, 20: 441-462.
Dmitrieva, N., et al., "The role of nerve growth factor in a model of visceral inflammation", Neuroscience, vol. 78, No. 2, 1997, pp. 449-459.
Dosen-Micovic, et. al., Bioorganic and Medicinal Chemistry, 2006, Elsevier, vol. 14, pp. 2887-2895.
Dougherty, P.M., et al. "Taxol-induced sensory disturbance is characterized by preferential impairment of myelinated fiber function in cancer patients", Pain, 2004, vol. 109, pp. 132-142.
Drug encyclopedia M., RLS 2001, pp. 572-573, articles "Morphine", "Morphine Sulfate".
Perret, D., et al., "Targeting voltage-gated calcium channels for neuropathic pain management", Neurotherapeutics: The Journal of the American Society for Experimental NeuroTherapeutics, vol. 6, Oct. 2009, pp. 679-692.
Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.
Dunlap, B., et al., "Chemotherapy-Induced Peripheral Neuropathy Measurement", The Journal of Supportive Oncology, 2006, vol. 4, 8, pp.
Dworkin R.H., "An Overview of Neuropathic Pain: Syndromes, Symptoms, Signs, and Several Mechanisms," The Clinical Journal of Pain 2002, vol. 18, pp. 343-349.
Dworkin, R.H. et a., "Recommendations for the Pharmacological Management of Neuropathic Pain: Literature Update", Mayo Clin. Proc., 2010, 85(3) (Suppl), S3-S14.
Effenberger, F., et al., Chern. Ber., 102(10), 3260-3267, 1969.
Eghbaldar, et al., "Substances aromatisantes separation chirale par chromatographie gazeuse" Parfums, Cosmetiques, Aromes, 104, pp. 71-78, 1992.

(56) References Cited

OTHER PUBLICATIONS

Eisenach, J. C., et al., Intrathecal, but not intravenous, clonidine reduces experimental thermal or capsaicin-induced pain and hyperalgesia in normal volunteers; Anesth Analg; 1998; 87: 591-596.
Entrena, J.M., et al., "Sigma-I receptors are essential for capsaicin-induced mechanical hypersensitivity: Studies with selective sigma-1 ligands and sigma-1 knockout mice", Pain, (2009), vol. 143, pp. 252-261.
Epilepsy [online], [retrieved on Nov. 20, 2007]. Retrieved from the Internet, URL; http://www.nim.nih.gov/medlineplus/ency/article/000694.htm>.
Stubblefield, et al., "Upper-Extremity Pain Disorders in Breast Cancer" (2006) Arch Phys Med Rehabil, vol. 87, Suppl 1, pp. S96-S99.
Falk et al. "Pain and Nociception: Mechanisms of Cancer-Induced Bone Pain", Journal Clinical Oncology, 2014, vol. 32, pp. 1647-1654.
Wickham, "Chemotherapy-Induced Peripheral Neuropathy: A Review and Implications for Oncology Nursing Practice" (2007) Clinical Journal of Oncology Nursing, vol. 11, No. 3, pp. 361-376.
Receveur, Jean-Marie, et al., "Synthesis and biological evaluation of conformationally restricted gabapentin analogues", Bioorganic & Medicinal Chemistry Letters, 9, 1999, pp. 2329-2334.
Forsyth, P.A., et al., "Prospective study of paclitaxel-induced peripheral neuropathy with quantitative sensory testing", Journal of Neuro-Oncology, 1997, vol. 35, pp. 47-53.
Friedman, J.E., et al., Altered expression of muscle glucose transporter GLUT -4 in diabetic fatty Zucker rats (ZDF/Drtfa), American Physiological Society, 1991, E782-E788.
Romero, L., et al., J. Pharmacological properties of S1RA, a new Sigma-1 receptor antagonist that inhibits neuropathic pain and activity-induced spinal sensitization. Br. J. Pharmacal. 2012; doi: 10.1111/j.1476-5381.
Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 f pp. 732-734.
Gentili, M., et al., Intra-articular morphine and clonidine produce comparable analgesia but the combination is not more effective, Br J Anaesth. 1997; 79 (5): 660-661.
Uchitel, O.D., et al., "Acute modulation of calcium currents and synaptic transmission by Gabapentinoids," Channels, 4:6, Nov./Dec. 2010, pp. 490-496.
Goblirsch, M.J., et al., "Biology of Bone Cancer Pain," Clin. Cancer Res. 2006' vol. 12 (20 Suppl.), pp. 6231s-6235s.
Goodman, et al., "The Pharmacological Basis of Therapeutics", 8th Ed.; 13-18., 1992.
Gordois, A., et al., "The Health Care Costs of Diabetic Peripheral Neuropathy in the U.S.", Diabetes Care, vol. 26, No. 6, Jun. 2003, pp. 1790-1795.
Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.
Gotub et al., "Molecular Classification of Cancer: Class Discovery and Class Prediction by Gene Expression Monitoring," Science, 286: 531-537, 1999.
Grahame-Smith, D.G., et al., Oxford textbook on clinical pharmacology and drug therapy M., "Meditsina", 2000, pp. 658-661, Chapter "Narcotic analgesic".
Gralla et al., "Cisplatin and Vindesine Combination Chemotherapy for Advanced Carcinoma of the Lung: A Randomized Trial Investigating Two Dosage Schedules," Annals of Internal Medicine, 1981, 95: 414-420.
Grover, S., et al., "Role of inflammation in bladder function and interstitial cystitis", Therapeutic Advances in Urology, 3(1), 2011, pp. 19-33.
Grunberg et al., "Incidence of Chemotherapy-Induced Nausea and Emesis after Modern Antiemetics," Cancer, 2004, 100(10: 2261-2268.
Guignard, et al., "Acute Opioid Tolerance: Intraoperative RemifentanilIncreases Postoperative Pain and Morphine Requirement," Anesthesiology, vol. 93 pp. 409-417 (2000).
Guitart et al., "Sigma receptors: biology and therapeutic potential," Psychopharmacology, 2004, 174: 301-319.
Haleblian, "Characterization of Habits and Crystalline Modification of Solids and Their Pharmaceutical Applications," Journal of Pharmaceutical Sciences, vol. 64, No. 8 pp. 1269-1288 (1975).
Hall et al., "Sedative, analgesic and cognitive effects of clonidine infusions in humans," British Journal of Anaesthesia, 2001, 86(1): 5-11.
Diaz, J.L., et al., "Synthesis and Biological Evaluation of the 1-Arylpyrazole Class of sigma 1 Receptor Antagonists: Identification of 4-{2-[5-Methyl-1-(naphthalen-2-y1)-1E-pyrazol-3-yloxy]ethyl}morpholine (S1RA, E-52862)", Journal of Medicinal Chemistry, (Oct. 11, 2012), vol. 55, No. 19, doi:10.1021/jm3007323, ISSN 0022-2623, pp. 8211-8224, XP055094581 [Y] 1-14,16 * abstract * * p. 8219, col. left, paragraphs 3-4 *.
Hancock, et al., "Characteristics and Significance of the Amorphous State in Phamnaceutical Systems," Journal of Phamnaceutical Sciences, vol. 86, No. 1 pp. 1-12 (1997).
Hanner et al. "Purification, molecular cloning, and expression of the mammalian sigmal-binding site", Proc. Natl. Acad. Sci. USA, 1996, 93: 8072-8077.
Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.
Harden, N., et al., "Unmet Needs in the Management of Neuropathic Pain", Journal of Pain and Symptom Management, 2003, 25, 5S, S12-S17.
Hartwig, J., "Synthesis, Structure, and Reactivity of a Palladium Hydrazonato Complex: A New Type of Reductive Elimination Reaction to FormC-N Bonds and Catalytic Arylation of Benzophenone Hydrazone", Angew. Chern. Int. Ed., 1998, vol. 37, No. 15, pp. 2090-2093.
Hayashi and Su, "Sigma-1 Receptor Ligands: Potential in the Treatment of Neuropsychiatric Disorders," CNS Drugs, 2004, 18(5): 269-284.
Hecht et al., "Prolonged Nausea and Vomiting after High Dose Chemotherapy and Autologous Peripheral Stem Cell Transplantation in the Treatment of High Risk Breast Carcinoma," Cancer, 1997, 79(9): 1698-1702.
Herrstedt et al., "Acute emesis: moderately emetogenic chemotherapy," Support Care Cancer, 2005, 13:97-103.
Hesketh et al., "Proposal for Classifying the Acute Emetognicity of Cancer Chemotherapy," Journal of Clinical Oncology, 1997, 15(1): 103-119.
Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).
Hileman, G.A., et al., "Response surface optimization of high dose pellets by extrusion and spheronization," International Journal of Pharmaceutics, 1993, vol. 100, pp. 71-79.
Hiranita, et al., "Reinforcing effects of sigma-receptor agonists in rats trained to self-administer cocaine," J Pharmacol Exp Ther. Feb. 2010; 332(2):515-524 (2010).
Horner, et al., "Azo-aryle and Phenazine aus primaren Arylamin-anionen durch Autoxydation", Chern. Ber, 96, pp. 786-793, 1963.
Hsu, et al., Toxic. Appl. Pharmac., vol. 73, No. 3, pp. 411-415, 1984.
Hudzik, "Sigma ligand-induced emesis in the Pigeon," Pharmacology Biochemistry and Behavior, 1991, 41: 215-217.
Hudzik et al., "Sigma-receptor-mediated emetic response in pigeons—agonists, antagonists and modifiers," European Journal of Pharmacology, 1993, 236: 279-287.
IASP Classification of Chronic Pain, 2002, 2nd edition, pp. 201-213.
Isakov "The problem of pain in oncology", Russian Medicinal Journal, 2000, vol. 17, pp. 723-727.

(56) References Cited

OTHER PUBLICATIONS

Isomers [on-line], [retrieved on Mar. 11, 2007]. Retrieved from the Internet, URL; http://chemed.chem.purdue.edu/genchem/topicreview/bp/1organic/isomers.html>.
Izenwasser, S., et al., "Characterization of kappa-opioid receptor binding in human insular cortex", Life Sciences, Pergamon Press, Oxford, GB, vol. 65, No. 9, Jul. 23, 1999, pp. 857-862.
Janicki, et al., "Detection of Antagonist Activity for Narcotic Analgesics in Mouse Hot-Plate Test" Pharmacol. Biochem. Behavior, 1979; 10(4); pp. 623-626.
Jordan et al., "Chemotherapy-induced nausea and vomiting: current and new standards in the antiemetic prophylaxis and treatment," European Journal of Cancer, 2005, 41: 199-205.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., "Binding to the sigma receptor" Neurotransmissions; 1991; 7(1); 1-5.
Dugowson, et al.; Phys. Med. Rehabil. Clin. N. Am. 2006, 17, 347-354.
Hellewell, S.B., et al., "A sigma-likebinding site in rat pheochromocytoma (PC12) cells: decreased affinity for (+)-benzomorphans and lower molecular weight suggest a different sigma receptor form from that of guinea pig brain," Brain Research, (1990) vol. 527, pp. 244-253.
Wang, "Opioid-induced hyperalgesia", Chinese Journal of Pain Medicine, 14(3), pp. 129-130 (2008).
Wantuch, C., et al., "Pharmacological validation of a model of cystitis pain in the mouse", Neuroscience Letters, 421, 2007, pp. 250-252.
Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.
Weetman, A.P., "Graves' hyperthyroidism: how long should antithyroid drug therapy be continued to achieve remission?," Nature Clinical Practice Endocrinology and Metabolism, vol. 2, No. 1, Jan. 2006, pp. 2-3.
Kadiroglu, A.K., et al., "The effect of venlafaxine HCl on painful peripheral diabetic neuropathy in patients with type 2 diabetes mellitus.", Journal of Diabetes and Its Complications Jul.-Aug. 2008 (Jul. 2008), vol. 22, No. 4, ISSN 1873-460X, pp. 241-245, XP002721925 [Y] 1-17 * Venlafaxine HCl is effective in the treatment of peripheral diabetic neuropathic pain *.
Kenakin, A., Pharmacology Primer, The Evolving Pharmacology of GPCR's, 2006, pp. 27-60.
Kerba, et al. Oct. 2010, Journal of Clinical Oncology, vol. 28, No. 33, pp. 4892-4897.
Herndon, et al.; "Management of Chronic Nonmalignant Pain with Nonsteroidal Antiinflammatory Drugs" Pharmacotherapy, 2008, 28(6), 788-805.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA- induced pain via PKC- and PKA-dependent phosphorylation of the NR1 subunit in mice", Br. J. Pharmacal., 2008, vol. 154, pp. 1125-1134.
Kim, et al., "Update on the Pathology and Diagnosis of Interstitial Cystitis/Bladder Pain Syndrome: A Review" Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2007, vol. 151 No. 1, pp. 69-75.
Koralewski et al., "Effectiveness of cyproheptadine in the management of delayed vomiting after cisplatin-based chemotherapy and the assessment of the influence of cyproheptadine on quality of life," Nowotwory. Journal of Oncology, 2000, 50(5): 499-503.
Kranz, H., et al., "Drug Release from MCC- and carrageenan-based pellets: Experiment and theory," European Journal of Pharmaceutics and Biopharmaceutics, 2009, vol. 73, pp. 302-309.
Hinz et al., "Dipyrone elicits substantial inhibition of peripheral cyclooxygenases in humans: new insights into the pharmacology of an old analgesic" FASEB Journal, 2007, 7, 2343-2351.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (Sep. 1, 2000), p. 389, (Sep. 1, 2000), XP027389705 [Y] 1-17. * Venlafaxine controlled release is effective in the treatment of pain *.
Kuruvilla et al., Arch Otolaryngol Head Neck Surg. Jan. 2009; 135(1): 101-105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 (2): 175-181.
LaBudde, et al., "The Synthesis of the Mono- and Dihydroxy Derivatives of 1,2,5,6-Dibenzanthracene Excreted by the Rabbit and of Other Hydroxylated Dibenzanthracene Derivatives", J. Am. Chem. Soc., 80, pp 1225-1236, 1958.
Werling et al., "A comparison of the binding profiles of dextromethorphan, memantine, fluoxetine and amitriptyline: Treatment of involuntary emotional expression disorder," Experimental Neurology 2007, 207: 248-257.
Langa, et al., "Generation and phenotypic analysis of sigma receptor type I (σ1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection," Journal of the American Chemical Society, 2002, vol. 124, No. 50, pp. 14834-14835, S1-S2.
Lau, et al. (2010) Electroacupuncture versus celecoxib for neuropathic pain in rat SNL model. Neuroscience 170 (2): 655-661.
Le Bars, D., et al., Animal models of nociception. Pharmacal. Rev. 2001; 53, 597-652.
Lee et al., "A Comprehensive Review of Opiod-Induced Hyperalgesia," Pain Physician, 2011m 14:145-161.
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265-266, 282-283.
Wild, S., et al., "Global Prevalence of Diabetes", Diabetes Care, vol. 27, No. 5, May 2004, pp. 1047-1053.
Li, et al., "Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al., "Synthesis and Structure-Antitumor Activity of 4,6-Diamino-1,2-Dihydro-2,2-Dimethyi-1-(Substituted Naphthyi-2)-1,3,5-Triazines", Chem. Res. Chinese Univ., 7(3), pp. 197-200, 1991.
Li, F., et al., "Taurine reverses neurological and neurovascular deficits in Zucker diabetic fatty rats," Neurobiology of Disease, vol. 22, 2006, pp. 669-676.
Lippinscot et al., "Chapter 28: Gastrointestinal and Antiemetic Drugs," <healtheappointments.com/chapter-28-gastrointestinal-and-antiemetic-drugs-essays/>.
Lowry, et al., "Protein measurement with the folin phenol reagent," J. Bio.Chem, 1951, vol. 193, pp. 265-275.
Luedtke et al., "Neuroprotective effects of high affinity sigma 1 receptor selective compounds," Brain Research, 2012, 1441: 17-26.
Luger N.M., et al., "Efficacy of systemic morphine suggests a fundarnen tal difference in the mechanisms that generate bone cancer vs. inflammatory pain", Pain 2002, vol. 99, pp. 397-406.
Luger, N.M., et al., "Bone Cancer Pain: From Model to Mechanism to Therapy", J. Pain and Symp. Manag. 2005, vol. 29 pp. 832-846.

(56) References Cited

OTHER PUBLICATIONS

Lytle, et al., "Effects of long-term corn consumption on brain serotonin and the response to electric shock," Science vol. 190, pp. 692-694 (1975).
Mantyh, "Bone cancer pain: From mechanism to therapy", Opin. Support. Palliat. Care, 2014, vol. 8, pp. 83-90.
Mao, J., "Opioid-induced abnormal pain sensitivity: implications in clinical opioid therapy," Pain. vol. 100 pp. 213-217 (2002).
Mar. 1, 2016 Fourth Office Action, issued in connection with Chinese Patent Application No. 201180065232.X, including English language translation.
Mar. 29, 2016 Office Action, issued in connection with Japanese Patent Application No. 2013-541369, including English translation.
Marks, D.M., et al., "Serotonin-Norepinephrine reuptake inhibitors for pain control: Premise andpromise", Current Neuropharmacology, 2009, 7, pp. 331-336 (Exhibit 189).
Maryanoff, B.E., et al., The Wittig Olefination Reaction and Modifications Involving Phosphoryl-Stabilized Carbanions. Stereochemistry, Mechanism, and Selected Synthetic Aspectsu, Chem. Rev., 1989, vol. 89, pp. 863-927.
Matsumoto et al., "Correlation between neuroleptic binding to sigma 1 and sigma 2 receptors and acute dystonic reactions," European Journal fo Pharmacology, 2000, 401: 155-160.
Wilkes, G. "Peripheral Neuropathy Related to Chemotherapy", Seminars in Oncology Nursing, 2007, vol. 23, 3. pp. 162-173.
McGill, J.B., et al., "13-Biocker use and diabetes symptom score: results from the GEMINI study", Diabetes, Obesity and Metabolism, vol. 9, No. 3, May 2007, pp. 408-417.
Mega, et al., Experimental Diabetes Research, Jan. 12, 2011, Diabetic Nephropathy Amelioration by a Low-Dose Sitagliptin in an Animal Model of Type 2 Diabetes (Zucker Diabetic Fatty Rat).
Mei, et al., "Receptor Modulation of Opioid Analgesia in the Mouse", J. Pharmacol Exp. Ther.; 2002; 300(4); pp. 1070-1074.
Menten, J., "Co-analgesics and adjuvant medication in opioid treated cancer pain", Eur. J. Cancer Supplement 2005, vol. 3, pp. 77-86.
Mielke et al., "Peripheral neuropathy: A persisting challenge in paclitaxel-based regimes," European Journal of Cancer, 2006, 42: 24-30.
Ming, L.C., "Screening Polymorphic Forms of Drug Substances by Using Generalized Crystallization Techniques," May 2007 (English language Translation of Abstract).
Moncada A., et al., Effects of serine/threonine protein phosphatase inhibitors on morphine-induced antinociception in the tail flick test in mice. Eur J Pharmacal. 2003; Mar. 28; 465(1-2): 53-60.
Mosandi, et al., "Stereoisomeric Flavor Compounds XLIV: Enantioselective Analysis of Some Important Flavor Molecules", J. High Resol. Chromatog 13(9), pp. 660-662, 1990.
Mouedden, et al., "Pharmacological evaluation of opioid and non-opioid analgesics in a murine bone cancer model of pain", Pharm. Biochem. And Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is a major contributor to the antihyperalgesic effect of antidepressants after peripheral nerve injury in the rat. Pain. 2012; 153(5): 990.
Nakazato A., et al., "Synthesis and SAR of 1-alkyl-2-phenylethylamine derivatives designed from N,Ndipropyl-4-methoxy-3-(2-phenylethoxy) phenylethylamine to discover ?1ligands", J. Med. Chem., (1999), vol. 42, pp. 3965-3970.
Narujo, Hiroyuki, et al., Cancer Pain Treatment—Clinical Oral Morphine Extended-Release Tablets (once/day), 5th, Pharma Medical, 2007, including English language translation.
National Cancer Institute. "Nausea and Vomiting" <www.cancer.gov/about-cancer/treatment/side-effects/nausea/nausea-pdg>.

Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.
Nieto, F.R., et al., "Tetrodotoxin inhibits the development and expression of neuropathic pain induced by paclitaxel in mice", Pain, 2008, vol. 137, pp. 520-531.
Niiyama, et al., "SB366791, a TRPV1 antagonist, potentiates analgesic effects of systemic morphine in a murine model of bone cancer pain", Br. J. Anaesth., 2009, vol. 102, pp. 251-258.
Noda, et al., "A Neuroactive Steroid, Dehydroepiandrosterone Sulfate, Attenuates The Development of Morphine Dependence: An Association with Sigma1 Receptors," Neuroscience 2001 Abstract, Presentation No. 668.4, Nov. 2001.
Nomura, M., et al., "Studies on drug dependence (Rept 322): Attenuation of morphine- and psychostimulants-induced place preference by sigma1 receptor agonist SA4503", Japanese Journal of Pharmacology, The Japanese Pharmacological Society, Kyoto, JP, vol. 79, No. suppl. 1, Jan. 1, 1999, p. 224P.
O'Brien, C. J., "Recycling the Waste: The Development of a Catalytic Witting Reaction", Agnew. Chem. Int. Ed. 2009, vol. 48, pp. 6836-6839.
Office Action and Search Report corresponding to Taiwanese Patent Application No. 100127236 (Translation) [undated].
Wilson, S. G., "The heritability of antinociception: common pharmacogenetic mediation of five neurochemically distinct analgesics," J Pharmacal Exp Ther. 2003; 304 (2): 547-559.
Official Action corresponding to Japanese Patent Application No. 2013-523580, dated Mar. 31, 2015.
Ohsawa, et al., "Effect of acute topical application of(+)-pentazocine on the mechanical allodynia in diabetic mice" Eur. J. Pharmacal., 2010, 641, pp. 49-53.
Olivar, T., et al., "Cyclophosphamide cystitis in mice: behavioural characterisation and correlation with bladder inflammation", European Journal of Pain, 3, 1999, pp. 141-149.
Oltman, C.L., et al., "Progression of vascular and neural dysfunction in sciatic nerves of Zucker diabetic fatty and Zucker rats", Am. J. Physiol. Endocrinol. Metab., vol. 289, 2005, pp. E113-E122.
Oltman, C.L., et al., "Vascular and neural dysfunction in Zucker diabetic fatty rats: a difficult condition to reverse", Diabetes, Obesity and Metabolism, vol. 10, 2008, pp. 64-74.
Oltman, et al., Treatment of Zucker diabetic fatty rats with AVE7688 improves vascular and neural dysfunction, Diabetes, Obesity and Metabolism, vol. 11, No. 3, 2009, pp. 223-233.
Winkler, et al., "Synthesis of Highly Functionalized Furanones via Aldol Reaction of 3-Silyloxyfurans", Organic Letters, vol. 7, No. 3, pp. 387-389, 2005.
Ongioco, C. D., et al., Alpha2-adrenergic receptors in human dorsal root ganglia: predominance of alpha2b and alpha2c subtype mRNSs, Anesthesiology 2000; 92 (4): 968-976.
Osipova, N.A., "Tramadol (Tramal) in the Treatment of Acute and Chronic Pain Syndromes," Russky Meditsinsky Zhurnal (Russian Medical Journal), Feb. 25, 2003, No. 4, Sections: Pulmonology: Selected Lectures for Family Physicians (Retrieved from the Internet: URL <rmj.ru/number.36.htm).
Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months.".
Owens et al., "Antiemetic efficacy of prochlorperazine, haloperidol and droperidol in cisplatin-induced emesis," Clinical Pharmacy 1984, 3: 167-170.
Pacharinsak, C., et al., "Animal Models of Cancer Pain", Comparative Medicine, 2008, vol. 58, No. 3, pp. 220-233.
Paice, J. A., "Clinical Challenges: Chemotherapy-induced Peripheral Neuropathy", Seminars in Oncology Nursing, 2009, vol. 25, N. 2, Suppl 1, pp. S8-S19.
Palmer et al., "Association between symptom distress and survival in outpatients seen in a palliative care cancer center," Journal of Pain and System Management, 2005, 29(6): 565-571.

(56) References Cited

OTHER PUBLICATIONS

Paquette et al., "The sigma-1 antagonist BMY-14802 inhibits L-DOPA abnormal involuntary movements by a WAY-100635-sensitive mechanism," Psychopharmacology 2009, 204(4): 743-754.
Park et al., "Mechanisms underlying chemotherapy-induced neurotoxicity and the potential for neuroprotective strategies," Current Medicinal Chemistry, 2008, 15: 3081-3094.
Hammack, et al., "Phase III evaluation of nortriptyline for alleviation of symptoms of cis-platinum-induced peripheral neuropathy" (2002) Pain, 98:195-203. (Abstract).
Petrie, C. et al., "A Novel Biotinylated Adenylate Analogue Derived from Pyrazolou3,4-D ¾ Pyrimidine for Labeling DNA Probes" Bioconjugate Chemistry, ACS, Washington, DC, US LNKD-DOI:10.1021/BC00012A011, vol. 2, No. 6, Nov. 1, 1991 (Nov. 1, 1991), pp. 441-446, XP0005727891SSN: 1043-1802.
Pirim, A., et al., "Addition of ketamine infusion to patient controlled analgesia with intravenous morphine after abdominal hysterectomy" Agri Jan. 2006; 18(1):52-58 Abstract.
Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.
Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (Mar. 1, 2006), vol. 29, No. 2, suppl, ISSN 0162-220X, pp. 39-47, XP009107315 [A] 1-16 * p. 41, col. R, paragraph 2 * * p. 42, col. R, paragraph 2 *.
Poncelet, A.N., "Risk factors, patterns of presentation, diagnosis, and treatment", Geriatrics, vol. 58, No. 6, Jun. 2003, pp. 16-18, 24-30.
Postma, T.J., et al., "Paclitaxel-induced neuropathy," Annals of Oncology, 1995, vol. 6, pp. 489-494.
Price, et al., J. Am. Chem. Soc., (2005), vol. 127, p. 5512.
Prodrug [online], [retrieved on Mar. 11, 2007. Retrieved from the Internet, URL; http://en.wikipedia.org/wiki/Prodrug>.
Puente, B., et al., "Sigma-1 receptors regulate activity-21 induced spinal sensitization and neuropathic pain after peripheral nerve injury", Pain, 2009, vol. 145, pp. 294-303.
Puskas, F., et al., Intrathecal clonidine and severe hypotension after cardiopulmonary bypass, Anesth Analg. 2003; 97 (5): 1251-1253.
Quasthoff, S., et al., "Chemotherapy-induced peripheral neuropathy," J Neural., 2002, vol. 249, pp. 9-17.
Radesca, et al., "Synthesis and Receptor Binding of Enantimeric N-Substituted cis-N-[2(3,4 Dishlorophenyl)ethyl]-2-(1-pyrrolidinyl) cyclohexylamines as High-Affinity σReceptor Ligands," J. Med. Chem., 1991, vol. 34, pp. 3058-3065.
Rao, R.D., et al., "Efficacy of Lamotrigine in the Management of Chemotherapy-induced Peripheral Neuropathy placebo-controlled trial, N01C3", Cancer; 2008, 112(12), 2802-2808.
Raynov, "Antiemetics: Side effects and reactions," Archive of Oncology, 2001, 9(3): 151-153.
Kest, et. al., Pharmacology Biochemistry, and Behavior, 1995, Pergamon, vol. 52, No. 1, pp. 175-178.
Reuben, S. S., et al., "Evaluation of efficacy of the perioperative administration of venlafaxine XR in the prevention of postrnastectorny pain syndrome", Journal of Pain and Syrnptorn Management, Feb. 2004, vol. 27, No. 2, pp. 133-139.
Rodriguez-Spong, B., et al., "General principles of pharmaceutical solid polymorphism: a supramolecular Perspective," Advanced Drug Delivery Reviews, vol. 56 (2004) pp. 241-274.
Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.
Roila et al., "Delayed emesis: moderately emetogenic chemotherapy," Support Care Cancer, 2005, 13:104-108.
Roos, et al., Radiotherapy and Oncology, 2003, vol. 67, pp. 207-212.
Rossiter, et al., "Copper (H)-Mediated Arylation with Aryl Boronic Acids for the N-Derivatization of Pyrazole Libraries," J. Comb. Chem., 2004, vol. 6, pp. 385-390, published on web Feb. 5, 2004.
Rouleau, A., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.
Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.
Rowinsky, E.K., et al., "Clinical Toxicities Encountered 24 with Paclitaxel (TAXOL)", Seminars in Oncology, 1993, vol. 20, No. 4, suppl. 3, pp. 1-15.
Sabetkasaie, M., et al., "Clonidine and guanfacine-induced antinociception in visceral pain: possible role of alpha2/I2 binding sites", European Journal of Pharmacology, Elsevier Science, NL, (Oct. 6, 2004), vol. 501, No. 1-3, doi:10.1016/J.EJPHAR.2004.08. 010, ISSN 0014-2999, pp. 95-101.
Wolf, S., et al., "Chemotherapy-induced peripheral neuropathy: Prevention and treatment strategies," European Journal of Cancer, 2008, vol. 44, issue 11, pp. 1507-1515.
Said, G., "Diabetic Neuropathy", Proceedings advanced studies in Medicine, vol. 1, No. 11, Dec. 2001, pp. 457-459.
Wu, et al., Regulatory Perspectives of Type II Prodrug Development and Time- Dependent Toxicity Management: Nonclinical Pharm/Tox Analysis and the Role of Comparative Toxicology, Toxicology, 236: 1-6, 2007.
Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15 * See abstract: imidazoline I2 receptor ligands have antinociceptic effect in acute pain *.
Samso, E., et al., Comparative assessment of the anaesthetic and analgesic effects of intramuscular and epidural clonidine in humans, Can J Anaesth. 1996; 43 (12): 1195-1202.
Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.
Sandford, M., et al., "Opioid Induced Hyperalgesia: Clinical Implications for the Pain Practitioner". Pain Physician 2009; 12:679-684
Sant et al., "The mast cell in interstitial cystitis: role in pathophysiology and pathogenesis," Urology, 69, Suppl 4A, 2007, pp. 34-40.
Schiff, et al., "Promotion' of microtubule assembly in vitro by taxol". Nature (1979) vol. 277 pp. 665-667.
Schetz et al., "A prototypical sigma-1 receptor antagonist protect against brain ischemia," Brain Research, 2007, 1181: 1-9.
Schlegel, T., et al., "Responsiveness of C-fiber nociceptors to punctate force-controlled stimuli in isolated rat skin: lack of modulation by inflammatory mediators and flurbiprofen" Neuroscience Letters, vol. 361, 2004, pp. 163-167.
Schoeffter, et al., "Functional, endogenously expressed 5-hydroxytryptamine 5-ht7 receptors in human vascular smooth muscle cells," British Journal of Pharmacology, 1996, vol. 117, pp. 993-994.
Schreiber, S., et al., "The antinociceptive effect of venlafaxine in mice is mediated through opioid and adrenergic mechanisms", Neuroscience Letters, Limerick, IE, (Jan. 1, 1999), vol. 273, doi: 10.1016/S0304-3940(99)00627-8, ISSN 0304-3940, pp. 85-88, XP003009174 [Y] 1-17 * Venlafaxine has antinociceptive effects and is effective for treating pain. *.
Seigel et al., "The control of chemotherapy-induced emesis," Annals of Internal Medicine, 1981: 95: 352-359.
Selwood et al., "Synthesis and biological evaluation of novel pyrazoles and indazoles as activators of the nitric oxide receptor, soluble guanylate cyclase," J. Med. Chem., 2001, 44:78-93.
Sevcik, M.A., et al., "JInti-NGF therapy profoundly reduces bone cancer pain and the accompanying increase in markers of peripheral and central sensitization", Pain 2005, vol. 115, pp. 128-141.
Shaw, et al., Proc. Soc. Exp. Biol. Med., (1983), vol. 173, No. 1, pp. 68-75.

(56) References Cited

OTHER PUBLICATIONS

Shen, D.M., et al., "Versatile and Efficient Solid-Phase Syntheses of Pyrazoles and Isoxazoles", Organic Letters, 2000, vol. 2, No. 18, pp. 2789-2792.
Shimizu, I., et al., "Effects of AH-9700, (+)-pentazocine, DTG and oxybutynin on micturition in anesthetized rats with acetone-induced cystitis", Life Sciences 69, 2001, pp. 1691-1697.
Shimoyama, E., et al., Integrative Medicine you Need to know now "Cancer and Integrative Medicine Palliative Medicine", Modern Physician, Nov. 2008, vol. 28, No. 11, pp. 1605-1607.
Shu, et al., "Parameter Effects on the Thermal Reaction of Cystine and 2,5-Dimethyl-4-hydroxy-3(2H)-furanone", ACS Symposium Letters, 409, pp. 229-241, 1989.
Shvidenko, K.V., et al., "Recyclization Reactions of 2-(1-Benzoylpyrrolidin- 2-Ylidene)Malononitrile", 2010, vol. 46, No. 1, pp. 56-60.
Siau, C., et al., "Dysregulation of Cellular Calcitt.rn Homeostasis in Chemotherapy-Evoked Painful Peripheral Neuropathy"; Anest:h Analg., 2006, 102(5), pp. 1485-1490.
Sierralta, F., et al., Alpha-Adrenoceptor and opioid receptor modulation of clonidine-induced antinociception, Br J Pharmacal. 1996; 119 (3): 551-554.
Silvererman, M., "Opioid Induced Hyperalgesia: Clinical Implications for the Pain Practitioner," Pain Physician. vol. 12, pp. 679-684 (2009).
Silvey et al., "A randomized comparison of haloperidol plus dexamethasone versus prochlorperazine plus dexamethasone in preventing nausea and vomiting in patients receiving chemotherapy for breast cancer," J Clin Oncol, 1988, 6:1397-1400.
Sima, A.A.F., "The heterogeneity of diabetic neuropathy", Frontiers in Bioscience, May 2008, pp. 4809-4816.
Sima, A.A.F., et al., "A comparison of diabetic polyneuropathy in Type II diabetic BBZDR/Wor rats and in Type I diabetic BBNVor rats", Diabetologia, vol. 43, 2000, pp. 786-793.
Smith, et al., "Paclitaxel-induced neuropathic hypersensitivity in mice: Responses in 1 0 inbred mouse strains," Life Sci., (2004), vol. 74, No. 21, pp. 2593-2604.
Smith and Wright, "Haloperidol: an alternative butyrophenone for nausea and vomiting prophylaxis in anesthesia," AANA Journal, 2005, 74: 273-275.
Smith, M.T., "Opioid-induced hyperalgesia, opioid rotation and opioid combinations," Acute Pain. vol. 10, pp. 199-200 (2008).
Snyder, et al., "Receptor Mechanisms in Antipsychotic Drug Action: Focus on Sigma Receptors," Journal of Neuropsychiatry, Winter 1989, vol. No. 1, pp. 7-15.
Sonal, G., et al., "Role of inflammation in bladder function and interstitial cystitis" Ther. Adv. Urol., (2011), vol. 3, No. 1, pp. 19-33.
Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
Non-Final Office Action dated Feb. 2, 2009 in related application U.S. Appl. No. 11/574,361 citing STN-search report JP10055048 (p. 8).
Strupp, et al., "Transdermal fentanyl during high-dose chemotherapy and autologous stem cell support" (2000) Oncology Reports, 7:659-661.
Wunsch, et al., "The σ1 Receptor Antagonist S1RA is a Promising Candidate for the Treatment of Neurogenic Pain". Journal Med. Chem. vol. 55, No. 19, pp. 8209-8210, 2012.
Su, et al., "The pharmacology of sigma-1 receptors" Pharmacology & Therapeutics, vol. 124, pp. 195-206, 2009.
Sussman, N., "SNRis versus SSRis: Mechanisms of action in treating depression and painful physical syrnptorns", Primary Care Companion J. Clin. Psychiatry, 2003, 5 (suppl 7), pp. 19-26.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.
Tanda, S., et al., "Pains Resistant to Opioids, and Countermeasures thereof–Including Peripheral Neuropathy Measures of Oxaliplatin", Pharmacy, Oct. 2007, vol. 58, No. 11, pp. 2947-2953 [inc. machine English language translation].
Polomano, R.C., et al., "Chemotherapy-evoked Painful Peripheral Neuropathy", Pain Medicine, 2001, vol. 2, No. 1, pp. 8-14.
Theoharides, T.C., "Mast cell involvement in interstitial cystitis: a review of human experimental evidence," Urology, (2001), vol. 57, No. 6, pp. 47-55.
Tietze, L., et al., "Improved Synthesis of (E)-3-Alkoxy- and (E)-3-Phenoxyacryloyl Chlorides". Synthesis, (11), 1079-1080, 1993.
Tramer and Walder, "Efficacy and adverse effects of prophylactic antiemetics during patient-controlled analgesia therapy: a quantitative systematic review," Anesth. Analg., 1999, 88:1354-1361.
Trescot et al., "Opioids in the Management of Chronic Non-Cancer Pain: An Update of American Society of the Interventional Pain Physicians' (ASIPP) Guidelines," Pain Physician. Opioids Special Issue: 11 pgs. S5-S62 (2008).
Tyers et al., "Mechanism of the anti-emetic activity of 5-HT3 receptor antagonists," Oncology, 1992, 49(4): 263-268.
Kuloor, et. al., Age and Aging, 2006, Oxford University Press, vol. 35, pp. 639-640.
Van De Merwe, J.P., et al., "Diagnostic criteria, classification, and nomenclature for painful bladder syndrome/interstitial cystitis: an ESSIG proposal", European Urology, 53, 2008, pp. 60-67.
Van Sickle et al., "Cannabinoids inhibit emesis through CB1 receptors in the brainstem of the ferret," Gastroenterology, 2001, 121:767-774.
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 2012, 32 Suppl. 1, pp. 3-10.
Venturello, C., "2-Arylazo-2, 5-dimethyl-3-oxo-2, 3-dihydrofurans, useful intermediates in the synthesis of 1- aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions 1: Organic and Bio-organic Chemistry, (1972-1999), 7, 681-685, 1978.
Vileikyte, L., et al., Psychological aspects of diabetic neuropathic foot complications: an overview, Diabetes/Metabolism Research and Reviews, 2004, vol. 20 (Suppl1), pp. S13-S18.
Vinik, A., et al., "Diabetic neuropathies: clinical manifestations and current treatment options". Nature Clinical Practice Endocrinology & Metabolism, (2006), 2(5):269-281.
Vippagunta, et al., "Crystalline solids," Advanced Drug Delivery Reviews, 48: 1-26, 2001.
Virmani, et al., Indian Journal of Chemistry, Section B: Organic Chemistry Including Medicinal Chemistry, vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database accession No. 705147, XP002605613 [X] 1-3, 9 * the whole document *.
Virmani, V. et al., "Methyl-{4-[5-(4-nitro-phenyl)-1-phenyl-1H-pyrazol-3-yl]-butyl}amine", Database Beilstein, Beilstein Institute for Organic Chemistry, Frankfurt-Main, DE, Database accession No. 706821, XP002605614 [X] 1-3, 9 * the whole document.
Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3, 9 * the whole document *.
Vorobeychik, et al., "Combination Therapy for Neuropathic Pain—A Review of Current Evidence," CNS Drugs, 2011, pp. 1-12.
Wagaw, S. et al., "A Palladium-Catalyzed Strategy For The Preparation of Indoles: A Novel Entry Into The Fischer Indole Synthesis", J. American Chemical Society, 1998, vol. 120, pp. 6621-6622.
Walker, et al., "Sigma Receptors: Biology and Function," Pharmacological Review, 1990, vol. 42, No. 4, pp. 355-402.

(56) References Cited

OTHER PUBLICATIONS

Quirion, et al., "A proposal for the classification of sigma binding sites," Trends Pharmacol. Sci., 1992 vol. 13, pp. 85-86.
Xiaoping, et al., "Involvement of the spinal NMDA receptor/PKCy signaling 12 pathway in the development of bone cancer pain", Brain Research, 2010, vol. 1335, pp. 83-90.
Xu et al., "Identification of the PGRMC1 protein complex as the putative sigma-2 receptor binding site," Nature Communications, 2001, 2:1-7.
Yaksh, T. L., Pharmacology of spinal adrenergic systems which modulate spinal nociceptive processing. Pharmacal Biochem Behav. 1985; 22(5): 845-858.
Yeretzian, et al., "Analysing the headspace of coffee by proton-transfer-reaction mass-spectrometry", Int J. Mass Spect, 223-224 (1-3), pp 115-139, 2003.
Zhang et al., "Further characterization of the effects of BMY 14802 on dopamine neuronal activity," Synapse, 1993, 15: 276-284.
Zheng, F.Y., et al. "The Response Of Spinal Microglia To Chemotherapy Evoked Painful Peripheral Neuropathies Is Distinct From That Evoked By Traumatic Nerve Injuries," Neuroscience, 2011, 176, pp. 447-454.
Telleria-Diaz, et al., "Spinal antinociceptive effects of cyclooxygenase inhibition during inflammation: involvement of prostaglandins and endocannabinoids". Pain, 2010, 148, pp. 26-35.
Office Action dated Mar. 18, 2013 in connection with Russian Patent Application No. 2010138634, filed Feb. 17, 2009.
International Preliminary Report of Patentability with Written Opinion of the International Searching Authority dated Aug. 24, 2010 in connection with International Application No. PCT/EP2009/001109.
European Search Report dated Feb. 1, 2005 in connection with priority European Application No. EP 04077421.8.
European Search Report dated Sep. 12, 2008 in connection with European Application No. EP08384006.
European Search Report dated Oct. 2, 2008 in connection with European Application No. EP 08380122.
European Search Report dated Feb. 5, 2010 in connection with European Application No. EP09382144.
European Search Report dated Apr. 14, 2010 in connection with European Application No. EP09382261.
European Search Report dated Apr. 19, 2010 in connection with European Application No. EP10382024.7.
European Search Report dated Jun. 16, 2010 in connection with European Application No. EP 10382023.
European Search Report dated Jul. 1, 2010 in connection with European Patent Application No. EP10382025.
European Search Report dated Oct. 1, 2010 in connection with European Application No. EP10382215.1.
Extended European Search report dated Oct. 22, 2010 by European Patent Office in connection with European Application No. EP 10 38 2148.
European Search Report dated Oct. 29, 2010 in connection with European Application No. EP10382136.
European Search Report dated Jan. 31, 2011 in connection with European Patent Application No. 10382326.6.
European Search Report dated Mar. 11, 2011 in connection with European Application No. EP10382330.8.
European Search Report dated Oct. 18, 2011 in connection with European Application No. EP11382157.3.
European Search Report dated May 3, 2013 in connection with European Patent Application No. EP13382140.
European Search Report dated Dec. 20, 2013 in connection with European Application No. EP13382246.0.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2010/068213.
International Preliminary Report of Patentability with Written Opinion of the International Searching Authority dated Feb. 12, 2013 in connection with international Patent Application No. PCT/EP2011/063583.
International Preliminary Report of Patentability with Written Opinion of the International Searching Authority dated Aug. 7, 2012 in connection with International Application No. PCT/EP11/51643.
International Preliminary Report of Patentability with Written Opinion of the International Searching Authority dated Mar. 15, 2016 in connection with International Applications No. PCT/EP2014/069370.
International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with International Application No. PCT/EP2005/009375.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Aug. 7, 2012 in connection with International Application No. PCT/EP2011/051644.
International Preliminary Report of Patentability with Written Opinion of the International Searching Authority dated Feb. 3, 2013 in connection with International Application No. PCT/EP2011/063286.
International Preliminary Report of Patentability with .Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.
International Preliminary Report of Patentability with Written Opinion of the International Searching Authority dated Jun. 26, 2012 in connection with International Application No. PCT/EP2012/059232.
International Preliminary Report of Patentability with Written Opinion of the International Searching Authority dated May 30, 2012 in connection with International Application No. PCT/EP2010/068256.
International Preliminary Report of Patentability with Written Opinion of the International Searching Authority dated Nov. 27, 2012 in connection with International Applications No. PCT/EP2011/058224.
International Preliminary Report of Patentability with Written Opinion of the International Searching Authority dated Oct. 20, 2015 in connection with International Application No. PCT/EP2014/057608.
International Search report dated Jul. 7, 2009 in connection with International Application No. PCT/EP2009/001109.
International Preliminary Report of Patentability with Written Opinion of the International Searching Authority dated Oct. 26, 2010 in connection with International Application No. PCT/EP2009/054974.
International Preliminary Report of Patentability with Written Opinion of the International Searching Authority dated Oct. 26, 2010 in connection with International Application No. PCT/EP2009/054981.

(56) References Cited

OTHER PUBLICATIONS

International Search Report dated Apr. 5, 2011 in connection with International Application No. PCT/EP2011/051644.
International Search Report dated Jan. 12, 2005 in connection with International Application No. PCT/EP2005/009375.
International Search Report dated Jun. 17, 2009 in connection with International Application No. PCT/EP2009/054974.
International Search report dated Oct. 31, 2014 in connection with International Application No. PCT/EP2014/069370.
International Search Report dated Jul. 24, 2009 in connection with International Application No. PCT/EP2009/054981.
International Search Report dated Nov. 25, 2010 in connection with International Application No. PCT/EP2010/061720.
International Search Report dated Mar. 8, 2011 in connection with International Applications No. PCT/EP2011/058224.
International Search Report dated Mar. 23, 2011 in connection with International Application No. PCT/EP2010/068213.
International Search Report dated May 4, 2011 in connection with International Application No. PCT/EP2011/051630.
International Search Report dated May 4, 2011 in connection with International Application No. PCT/EP2010/068256.
International Search Report dated Aug. 31, 2011 in connection with International Application No. PCT/EP2011/063583.
International Search Report dated Sep. 21, 2011 in connection with International Application No. PCT/EP2011/058633.
International Search Report dated Jan. 16, 2012 in connection with International Application No. PCT/EP2001/071583.
International Search Report dated Jan. 31, 2012 in connection with International Application No. PCT/EP2011/063286.
International Search Report dated Mar. 13, 2012 in connection with International Application No. PCT/EP2011/071584.
International Search Report dated Jun. 26, 2012 in connection with International Application No. No. PCT/EP12/59232.
International Search Report dated Mar. 6, 2014 in connection with International Application No. PCT/EP2014/057608.
International Search report dated Sep. 17, 2014 in connection with International Application No. PCT/EP2014/063360.
International Search Report dated Feb. 25, 2015 in connection with International Application No. PCT/EP2014/077996.
González-Cano et al., "Receptors Are Involved in the Visceral Pain Induced by Intracolonic Administration of Capsaicin in Mice", Anesthesiology, 2013; 118:691-700.

\* cited by examiner

SIGMA LIGANDS FOR USE IN THE PREVENTION AND/OR TREATMENT OF POST-OPERATIVE PAIN

RELATED APPLICATIONS

This application is a §371 national stage of PCT International Application No. PCT/EP2011/051643, Feb. 4, 2011, claiming priority of European Patent Application No. EP 10 382 024.7, filed Feb. 4, 2010, the contents of each of which are hereby incorporated by reference into this application.

FIELD OF THE INVENTION

The present invention relates to the use of sigma receptor ligands in the prevention and/or treatment of pain developed as a consequence of surgery.

BACKGROUND

The treatment of pain conditions is of great importance in medicine. There is currently a world-wide need for additional pain therapy. The pressing requirement for a specific treatment of pain conditions is documented in the large number of scientific works that have appeared recently in the field of applied analgesics.

PAIN is defined by the International Association for the Study of Pain (IASP) as "an unpleasant sensory and emotional experience associated with actual or potential tissue damage, or described in terms of such damage" (IASP, Classification of chronic pain, $2^{nd}$ Edition, IASP Press (2002), 210). Although it is a complex process influenced by both physiological and psychological factors and is always subjective, its causes or syndromes can be classified. Pain can be classified based on temporal, aetiological or physiological criteria. When pain is classified by time, it can be acute or chronic. Aetiological classifications of pain are malignant or non-malignant. A third classification is physiological, which includes nociceptive pain (results from detection by specialized transducers in tissues attached to A-delta and C-fibres), that can be divided into somatic and visceral types of pain, and neuropathic pain (results from irritation or damage to the nervous system), that can be divided into peripheral and central neuropathic pain. Pain is a normal physiological reaction of the somatosensory system to noxious stimulation which alerts the individual to actual or potential tissue damage. It serves a protective function of informing us of injury or disease, and usually remits when healing is complete or the condition is cured. However, pain may result from a pathological state characterized by one or more of the following: pain in the absence of a noxious stimulus (spontaneous pain), increased duration of response to brief stimulation (ongoing pain or hyperpathia), reduced pain threshold (allodynia), increased responsiveness to suprathreshold stimulation (hyperalgesia), spread of pain and hyperalgesia to uninjured tissue (referred pain and secondary hyperalgesia), and abnormal sensations (e.g., dysesthesia, paresthesia).

Over twenty million patients have surgical procedures each year. Postsurgical pain (interchangeably termed, post-incisional pain), or pain that occurs after surgery or traumatic injury, is a serious and often intractable medical problem. Pain is usually localized within the vicinity of the surgical site. Post-surgical pain can have two clinically important aspects, namely resting pain, or pain that occurs when the patient is not moving and mechanical pain which is exacerbated by movement (coughing/sneezing, getting out of bed, physiotherapy, etc.). The major problem with post-surgical pain management for major surgery is that the drugs currently used have a variety of prominent side effects that delay recovery, prolong hospitalization and subject certain vulnerable patient groups to the risk of serious complications.

The three major classes of pharmaceutical drugs used to treat post-surgical pain are the opioid analgesics, local anesthetics, and the non-steroidal anti-inflammatory drugs (NSAID). Two of these classes of drugs, the opioid analgesics and NSAIDs, are typically administered systemically while the local anesthetics (e.g. channel blockers) are administered non-systemically during surgery.

The systemic administration of drugs to relieve pain after surgery is frequently inadequate. For example, systemic administration of opioids after surgery may cause nausea, the inhibition of bowel function, urinary retention, inhibition of pulmonary function, cardiovascular effects, and sedation.

"Post-surgical pain" (interchangeably termed "post-operative", "post-incisional" or "posttraumatic pain") refers to pain arising or resulting from an external trauma or injury such as a cut, puncture, incision, tear, or wound into tissue of an individual (including those that arise from all surgical procedures, whether invasive or non-invasive). As used herein, "post-surgical pain" does not include pain that occurs without an external physical trauma. In some embodiments, post-surgical pain is internal or external pain, and the wound, cut, trauma, tear or incision may occur accidentally (as with a traumatic wound) or deliberately (as with a surgical incision). Infections and/or physical or chemical injuries affecting the wound area can exacerbate and prolong post-surgical pain. As used herein, "pain" includes nociception and the sensation of pain, and pain can be assessed objectively and subjectively, using pain scores and other methods, e.g., with protocols well-known in the art. Post-surgical pain, as used herein, includes resting (also known as spontaneous, persistent or ongoing) pain and evoked pain (pain evoked by stimulation). Evoked pain can be classified as allodynia (i.e., pain due to a stimulus that does not normally provoke pain) and hyperalgesia (i.e., increased response to a stimulus that is normally painful). Stimuli can be thermal or mechanical (tactile) in nature. Mechanical and/or thermal allodynia and/or hyperalgesia can occur in the primary wound area (i.e., primary allodynia or hyperalgesia) or expand to adjacent and surrounding areas that become sensitized (i.e., secondary allodynia or hyperalgesia). Therefore, the pain is characterized by thermal hypersensitivity, mechanical hypersensitivity and/or resting pain (e.g. pain in the absence of external stimuli). Hyperpathia, characterized by an abnormally painful reaction to a stimulus, especially a repetitive stimulus, as well as an increased threshold. Hyperpathia may occur with allodynia, hyperesthesia, hyperalgesia, or dysesthesia, and faulty identification and localization of the stimulus, delay, radiating sensation, and after-sensation may be present, and the pain is often explosive in character. The pain can be primary (e.g., resulting directly from the pain-causing event) or secondary pain (e.g., pain associated with, but not directly resulting, from the pain-causing event). Further, the pain can be acute or chronic. Acute pain results from the external trauma (cut, puncture, incision, tear, or wound), including that arising from all surgical procedures, and can be mild and last seconds, minutes or hours, or it can be severe and last for weeks or months. In most cases, acute pain does not last longer than three months, and it disappears when the underlying cause of pain (e.g., the wound) has been cured or has healed. Unrelieved acute pain, however, might lead to chronic pain. Chronic pain (also known as persistent pain) usually lasts longer than three months, beyond the healing period of tissue damage. Chronic pain normally originates with the initial trauma/injury but persists despite the fact that the injury has healed and no new tissue injury occurs. Pain signals remain active in the nervous system for weeks, months, or years. Physical effects include tense muscles, limited mobility, sleep disturbances and changes in appetite. Emotional effects include depression, anger, anxiety and fear of re-injury. Such emotional effects can hinder a person's ability to return to normal work or leisure activities. Post-surgical pain can also be divided into "superficial" and "deep", and deep pain into "deep somatic" and "visceral". Superficial pain comes from the damaged skin or superficial tissues and is sharp, well-defined and clearly localized. Deep somatic pain comes from injured ligaments, tendons, bones, blood vessels, fasciae and muscles, and is dull, aching, poorly-localized. Visceral pain originates in the injured viscera (organs) and is usually more aching or cramping than somatic pain. Visceral pain may be well-localized, but often it is extremely difficult to locate, and several visceral regions produce "referred" pain when injured, where the sensation is located in an area completely unrelated to the site of injury. Post-surgical pain can also be neuropathic (i.e., neuropathic pain) in nature as the nervous system becomes injured. Peripheral neuropathic pain occurs when the lesion affects the peripheral nervous system (e.g., peripheral nerves, nerve roots and/or ganglia) and thus peripheral neuropathy takes place. Nerve damage by surgery can also result in nerve inflammation (neuritis) and neuralgia (pain in the distribution of the nerves). Central neuropathic pain may occur when the lesion affects the central nervous system (e.g., brain, cerebellum, spinal cord). Pain can result from neuroma (also known as "pseudoneuroma") formation (e.g., traumatic neuroma following nerve injury as a result of surgery) that typically occurs at the end of injured nerve fibres as a form of ineffective, unregulated nerve regeneration commonly near a scar, either superficially (skin, subcutaneous fat) or deep (e.g., after a cholecystectomy). Pain from deafferentation can also occur if injured or axotomized nerve fibres degenerate thus completely or partially interrupting afferent nerve impulses. Causalgia, a syndrome of sustained burning pain, allodynia, and hyperpathia after a traumatic nerve lesion, often combined with vasomotor and sudomotor dysfunction and later trophic changes can also happen. In fact, pain can arise from any tissue or part of the body where external trauma or injury such as a cut, puncture, incision, tear, or wound into tissue of an individual (including those that arise from all surgical procedures, whether invasive or non-invasive) occurs. Finally, pain can differ in quantity (e.g., mild, moderate, severe) and quality (e.g., aching, burning, tingling, electrical, stabbing), it can include abnormal sensations (e.g., dysesthesia, paresthesia) and it can be continuous, intermittent or oscillating in intensity.

Different animal models and studies on postoperative incisional pain are reported in the state of the art (T. J. Brennan et al. Pain 1996, 64, 493-501; P. K. Zahn et al. Regional Anesthesia and Pain Medicine 2002, Vol. 27, No 5 (September-October), 514-516).

Finally, it is important to emphasize that there is a need to provide a new form of prevention and/or treatment of post-surgical acute and chronic pain, allodynia, hyperalgesia and abnormal sensations secondary to nerve (peripheral neuropathy) and tissue (superficial and deep somatic and visceral) injury developing during and/or after surgery.

BRIEF DESCRIPTION OF THE INVENTION

The inventors of the present invention have surprisingly found and demonstrated that the administration of sigma receptor ligands is highly effective for preventing or treating the pain associated to a surgery. This benefit of the invention is more evident when the sigma ligand is specifically a sigma receptor antagonist, preferably in the form of a (neutral) antagonist, an inverse agonist or a partial antagonist.

Therefore, one aspect of the present invention relates to a sigma ligand for use in the prevention and/or treatment of pain developed as a consequence of surgery.

In a preferred embodiment, said sigma ligand has the general formula (I):

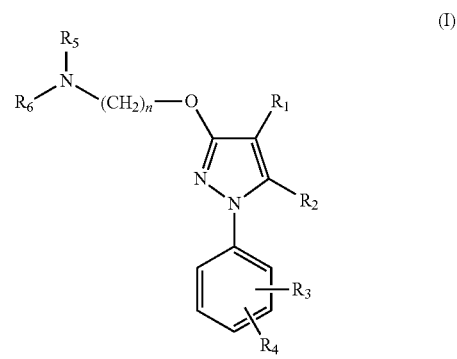

wherein
  $R_1$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
  $R_2$ is selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
  $R_3$ and $R_4$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together they form an optionally substituted fused ring system;
  $R_5$ and $R_6$ are independently selected from the group formed by hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)$—$R_8$, —$NR_8R_9$, —$NR_8C(O)R_9$, —$NO_2$, —$N=CR_8R_9$, and halogen, or together form, with the nitrogen atom to which they are attached, a substituted or unsubstituted, aromatic or non-aromatic heterocyclyl group;

n is selected from 1, 2, 3, 4, 5, 6, 7 and 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, and halogen;

or a pharmaceutically acceptable salt, isomer, prodrug or solvate thereof.

In another preferred embodiment, the sigma ligand has the general formula (II):

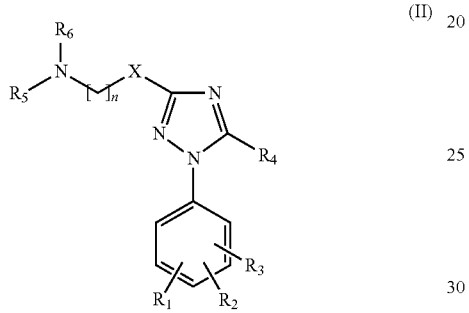

(II)

wherein $R_1$, $R_2$ and $R_3$ are independently selected from hydrogen, halogen, hydroxyl, alcoxyl, substituted or unsubstituted alkyl, cyano, $NR^aR^b$, $NHCONR^c$, $NHSO_2R^d$, COOH, $COOR^e$, wherein $R^a$ is hydrogen or alkyl and $R^b$, $R^c$, $R^d$ and $R^e$ are independently an alkyl;

$R^4$ is selected from hydrogen, substituted or unsubstituted alkyl, substituted or unsubstituted cycloalkyl, and substituted or unsubstituted, aromatic or non-aromatic heterocyclyl;

$R_5$ and $R_6$ are independently a substituted or unsubstituted alkyl or form, together with the nitrogen atom to which they are attached, a substituted or unsubstituted, aromatic or non-aromatic heterocyclyl group;

X is selected from —S—, —SO—, —SO$_2$— and O; and n is an integer selected from 1, 2, 3, 4, 5, 6, 7 and 8, or a pharmaceutically acceptable salt, isomer, prodrug or solvate thereof.

In still another preferred embodiment, the sigma ligand has the general formula (III):

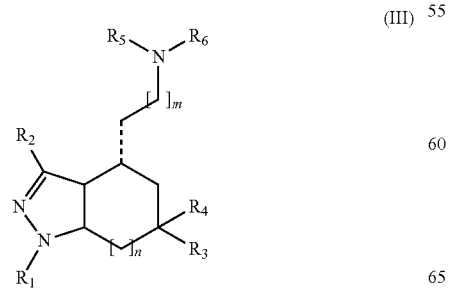

(III)

wherein $R_1$ is selected from the group formed by hydrogen, substituted or unsubstituted alkyl, substituted or unsubstituted cycloalkyl, substituted or unsubstituted, aromatic or non-aromatic heterocyclyl, substituted or unsubstituted aryl, substituted or unsubstituted arylalkyl, and substituted or unsubstituted heterocyclylalkyl;

$R_2$ is selected from the group formed by hydrogen, substituted or unsubstituted alkyl, substituted or unsubstituted cycloalkyl, substituted or unsubstituted alkoxy, substituted or unsubstituted aryl, substituted or unsubstituted, aromatic or non-aromatic heterocyclyl, substituted or unsubstituted arylalkyl, and substituted or unsubstituted heterocyclylalkyl;

$R_3$ and $R_4$ are independently selected from the group formed by hydrogen, substituted or unsubstituted alkyl, substituted or unsubstituted cycloalkyl, substituted or unsubstituted, aromatic or non-aromatic heterocyclyl, substituted or unsubstituted aryl, substituted or unsubstituted arylalkyl and substituted or unsubstituted heterocyclylalkyl or, together, $R_3$ and $R_4$ form a 3 to 6 substituted or unsubstituted member ring;

$R_5$ and $R_6$ are independently selected from the group formed by hydrogen, substituted or unsubstituted alkyl, substituted or unsubstituted cycloalkyl, substituted or unsubstituted, aromatic or non-aromatic heterocyclyl, substituted or unsubstituted aryl, substituted or unsubstituted arylalkyl and substituted or unsubstituted heterocyclylalkyl or, $R_5$ and $R_6$ together, form a substituted or unsubstituted, aromatic or non-aromatic heterocyclyl having 3 to 7 atoms in the ring;

n is selected from 0, 1 and 2;

m is selected from 0, 1, 2, 3 and 4;

the dotted line ----- is either a single or a double bond;

with the proviso that when $R_1$ is phenyl, $R_2$ is H, the dotted line ------ is a double bond, m is 1, and $R_5$ and $R_6$ form a 2,5-dioxopyrrolidine or a 5-ethoxy, 2-oxopyrrolidine; then $R_3$ and $R_4$ are not both at the same time H or methyl;

or a pharmaceutically acceptable salt, isomer, prodrug or solvate thereof.

Another aspect of this invention refers to the use of sigma ligand as defined above for the manufacture of a medicament for the prevention and/or treatment of pain developed as a consequence of surgery.

Another aspect of the invention is a method of treatment of a patient suffering from pain developed as a consequence of surgery, or likely to suffer pain as a result of a surgical treatment, which comprises administering to the patient in need of such a treatment or prophylaxis a therapeutically effective amount of a sigma ligand as defined above.

These aspects and preferred embodiments thereof are additionally also defined in the claims.

Figure 3:
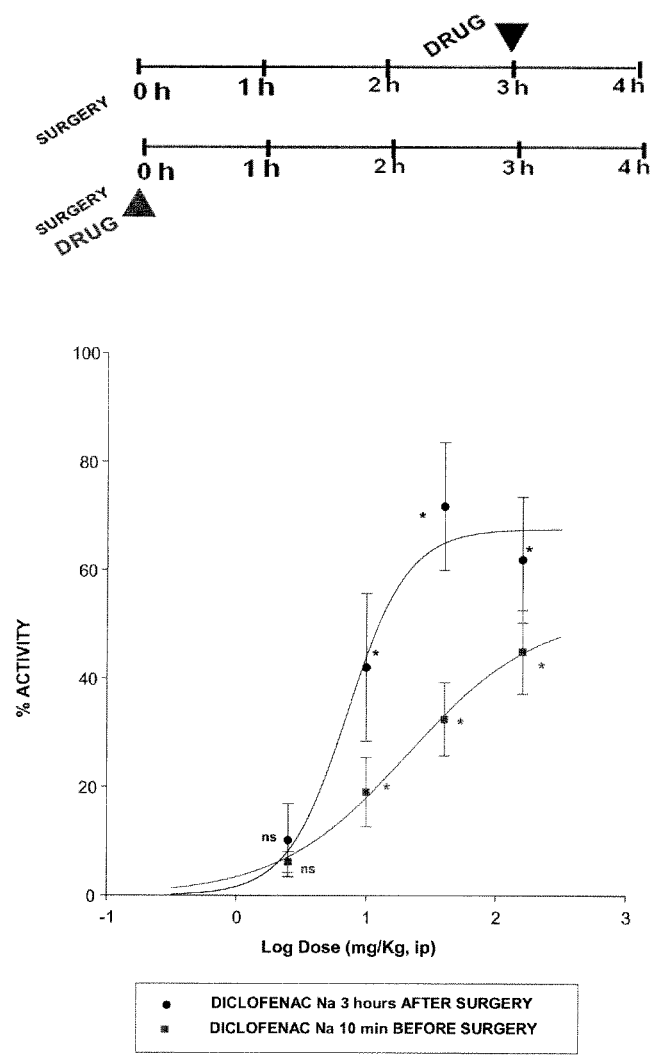

FIG. 3: Treatment vs preventive approach in mechanical allodynia. Comparative results of mechanical allodynia obtained with sodium diclofenac, commonly used for the post-surgical pain treatment, administered before (prevention) and after (treatment) surgery in the ipsilateral (operated) hindpaw of rats [−10 min: administration i.p. of the compound (preventive); 0 h: surgery; 3 h: administration i.p. of the compound (treatment); 4 h: mechanical allodynia assessment; *: significant differences (p<0.05); ns: non-significant differences (p>0.05); n=10].

Figure 4:
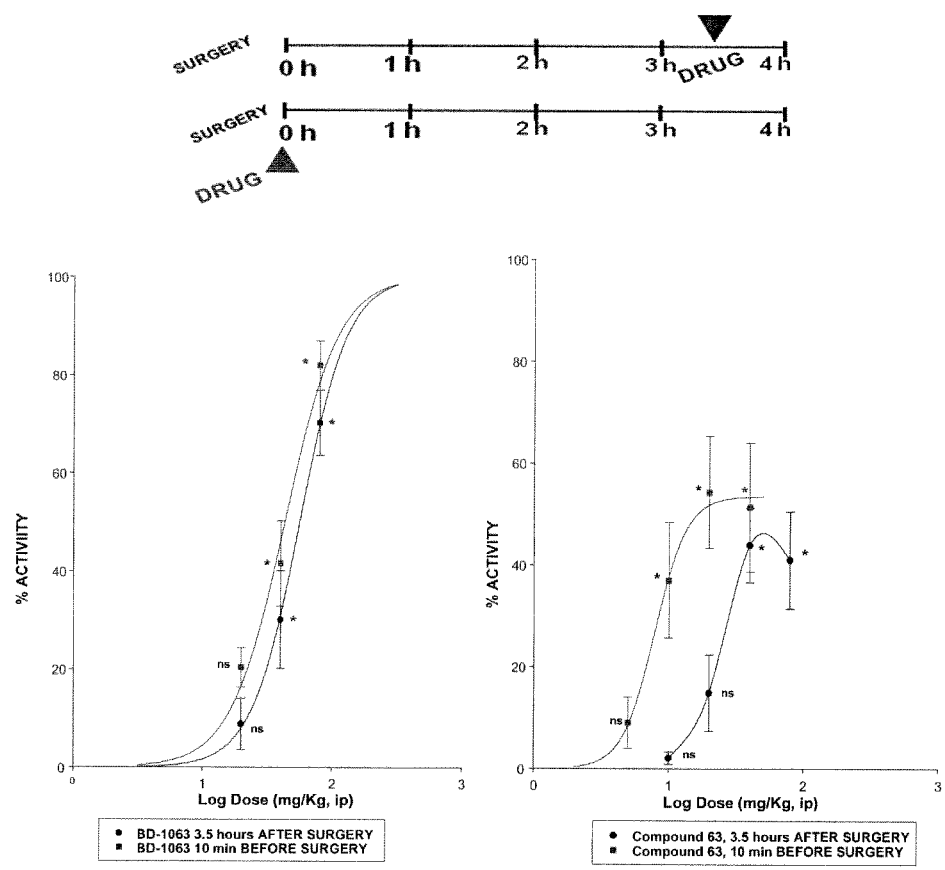

FIG. 4: Treatment vs preventive approach in mechanical allodynia. Comparative results of mechanical allodynia for BD-1063 and compound 63 administered before (prevention) and after (treatment) surgery in the ipsilateral (operated) hindpaw of rats [−10 min: administration i.p. of the compound (preventive); 0 h: surgery; 3.5 h: administration i.p. of the compound (treatment); 4 h: mechanical allodynia assessment; *: significant differences (p<0.05); ns: non-significant differences (p>0.05); n=10].

Figure 5:
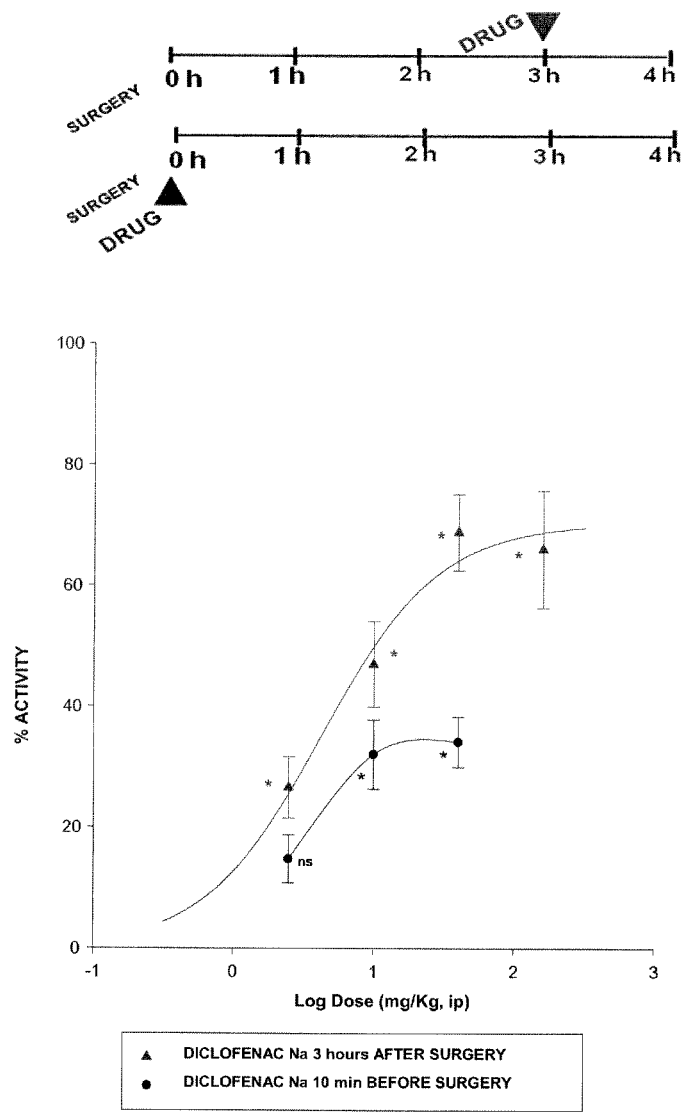

FIG. 5: Treatment vs preventive approach in thermal hyperalgesia. Comparative results of thermal hyperalgesia obtained with sodium diclofenac, commonly used for the post-surgical pain treatment, administered before (prevention) and after (treatment) surgery in the ipsilateral (operated) hindpaw of rats [−10 min: administration i.p. of the compound (preventive); 0 h: surgery; 3 h: administration i.p. of the compound (treatment); 4 h: thermal hyperalgasia assessment; *: significant differences (p<0.05); ns: non-significant differences (p>0.05); n=10].

Figure 6:
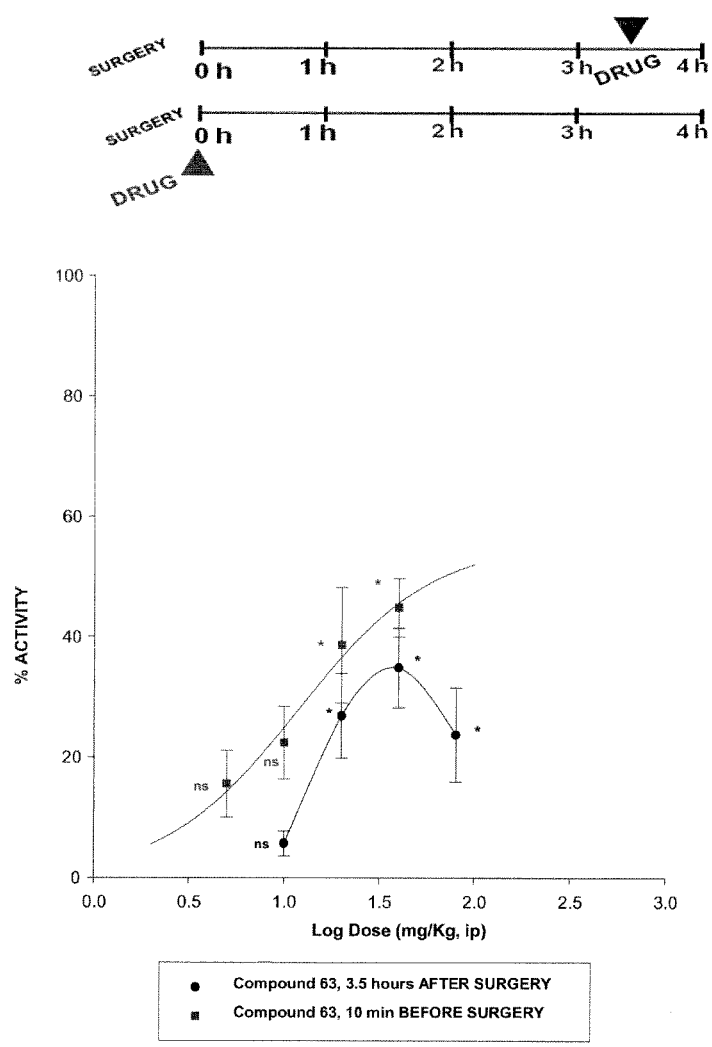

FIG. 6: Treatment vs preventive approach in thermal hyperalgesia. Comparative results of thermal hyperalgesia for compound 63 administered before (prevention) and after (treatment) surgery in the ipsilateral (operated) hindpaw of rats [−10 min: administration i.p. of the compound (preventive); 0 h: surgery; 3.5 h: administration i.p. of the compound (treatment); 4 h: thermal hyperalgasia assessment; *: significant differences (p<0.05); ns: non-significant differences (p>0.05); n=10].

DETAILED DESCRIPTION OF THE INVENTION

In the context of the present invention, the following terms have the meaning detailed below.

"Alkyl" refers to a straight or branched hydrocarbon chain radical consisting of 1 to 12 carbon atoms, containing no unsaturation, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkyl radicals have from 1 to 6 carbon atoms. If substituted by aryl, it corresponds to an "Arylalkyl" radical, such as benzyl or phenethyl. If substituted by heterocyclyl, it corresponds to a "Heterocyclylalkyl" radical.

"Alkenyl" refers to a straight or branched hydrocarbon chain radical consisting of 2 to 12 carbon atoms, containing at least one unsaturation, and which is attached to the rest of the molecule by a single bond. Alkenill radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkenyl radicals have from 2 to 6 carbon atoms.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple aromatic ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —OR$_a$, where R$_a$ is an alkyl radical as defined above, e.g., methoxy, ethoxy, propoxy, etc.

"Amino" refers to a radical of the formula —NH$_2$, —NHR$_a$, or —NR$_a$R$_b$, optionally quaternized, methylamino, ethylamino, dimethylamino, diethylamino, propylamino, etc.

"Halogen", "halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals.

Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a sigma ligand, in particular a prodrug of a compound of formulae (I), (II) or (III), is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The sigma ligands, in particular the compounds of formulae (I), (II) or (III), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As used herein, the terms "treat", "treating" and "treatment" include the eradication, removal, reversion, alleviation, modification, or control of pain induced by a surgical operation, after the pain onset.

As used herein, the terms "prevention", "preventing", "preventive" "prevent" and prophylaxis refer to the capacity of a therapeutic to avoid, minimize or difficult the onset or development of a disease or condition before its onset, in this case pain induced by a surgical operation.

Therefore, by "treating" or "treatment" and "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, e.g., prevented from happening, or stopped, e.g., terminated, such that the subject no longer experiences the condition. As such, the present method includes both preventing and managing acute and chronic pain induced by a surgical operation, including superficial and/or deep pain secondary to surgical tissue injury, and peripheral neuropathic pain, neuralgia, allodynia, causalgia, hyperalgesia, hyperesthesia, hyperpathia, dysesthesia, paresthesia, neuritis or neuropathy, secondary to surgical nerve injury.

As used herein, the terms "sigma ligand" or "sigma receptor ligand" refer to any compound binding to the sigma receptor. As stated previously, the sigma ligand is preferably a sigma receptor antagonist in the form of a (neutral) antagonist, an inverse agonist or a partial antagonist.

An "agonist" is defined as a compound that binds to a receptor and has an intrinsic effect, and thus, increases the basal activity of a receptor when it contacts the receptor. An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding. A "partial antagonist" is defined as a compound that binds to the receptor and generates an antagonist response; however, a partial antagonist does not generate the full antagonist response. Partial antagonists are weak antagonists, thereby blocking partially the action of an agonist or inverse agonist on the receptor.

An "inverse agonist" is defined as a compound that produces an effect opposite to that of the agonist by occupying the same receptor and, thus, decreases the basal activity of a receptor (i.e., signalling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist.

"The sigma receptor/s" as used in this application is/are well known and defined using the following citation: "this binding site represents a typical protein different from opioid, NMDA, dopaminergic, and other known neurotransmitter or hormone receptor families" (G. Ronsisvalle et al, Pure Appl. Chem. 73, 1499-1509 (2001)). Pharmacological data based on ligand binding studies, anatomical distribution and biochemical features distinguish at least two subtypes of σ receptors (R. Quiron et al., Trends Pharmacol. Sci. 13, 85-86 (1992); M. L. Leitner, Eur. J. Pharmacol. 259, 65-69 (1994); S. B. Hellewell and W. D. Bowen; Brain Res. 527, 244-253 (1990)) (G. Ronsisvalle et al. Pure Appl. Chem. 73, 1499-1509 (2001)). The protein sequences of the sigma receptors (Sigma 1 (σ1) and Sigma 2 (σ2)) are known in the art (e.g. Prasad, P. D. et al., J. Neurochem. 70 (2), 443-451 (1998)). They show a very high affinity to various analgesics (e.g. pentazocine).

"Compound/s binding to the sigma receptor" or "sigma ligand" as used in this application is/are defined as a compound having an $IC_{50}$ value of ≤5000 nM, more preferably ≤1000 nM, more preferably ≤500 nM on the sigma receptor. More preferably, the $IC_{50}$ value is ≤250 nM. More preferably, the $IC_{50}$ value is ≤100 nM. Most preferably, the $IC_{50}$ value is ≤50 nM, Additionally, the wording "Compound/s binding to the sigma receptor", as used in the present application is defined as having at least ≥50% displacement using 10 nM radioligand specific for the sigma receptor (e.g. preferably [$^3$H]-(+)pentazocine) whereby the sigma receptor may be any sigma receptor subtype. Preferably, said compounds bind to the sigma-1 receptor subtype.

Compounds binding to the sigma receptor, generally also referred to as sigma ligands, are well known in the art. Many of them are encompassed by the "Compound/s binding to the sigma receptor" definition above. Although there are many known uses for sigma ligands, such as antipsychotic drugs, anxiolytics, antidepressants, stroke treatment, antiepileptic drugs and many other indications, including antimigraine and general pain, there is no mention in the art of these compounds as useful for the prevention and/or treatment of pain developing as a consequence of surgery.

Table 1 lists some sigma ligands known in the art (i.e. having an $IC_{50}$≤5000 nM). Some of these compounds may bind to the sigma-1 and/or to the sigma-2 receptor. These sigma ligands also include their respective salts, bases, and acids.

TABLE 1

| | |
|---|---|
| (−)-Cyanopindolol hemifumarate | Cutamesine hydrochloride |
| (−)-(1R,2S)-cis-N-[2-(3,4-Dichlorophenyl)ethyl]-2-pyrrolidinocyclohexylamine | Cyclobenzaprine HCl |
| (−)-1-[1-(3-Chlorophenyl)pyrrolidin-2-ylmethyl]-4-(2-phenylethyl)piperazine | Cycloheximide |
| (−)-Sparteine sulfate pentahydrate | Cyproheptadine HCl |
| (+)-Himbacine | Darrow Red HCl |
| (±)-1-Cyclohexyl-4-[3-(5-methoxy-1,2,3,4-tetrahydronaphthalen-1-yl)propyl]piperazine | Demecarium Bromide |
| (1S,5R)-3-[2-(2-Adamantyl)ethyl]-1,8,8-trimethyl-3-azabicyclo[3.2.1]octane hydrochloride | Denatonium Benzoate |
| (2-Dibutylamino-Ethyl)-Carbamic Acid 2-(4-Benzofuran-2-Ylmethyl-Piperazin-1-Yl)-Ethyl Ester | Deptropine Citrate |

TABLE 1-continued

| | |
|---|---|
| (4-[1,2,3]Thiadiazol-4-Yl-Benzyl)-Carbamic Acid 1-(3-Methoxy-2-Nitro-Benzyl)-Piperidin-3-Ylmethyl Ester | Desloratadine |
| (4aalpha,8aalpha)-6-(4-Fluorophenyl)-2-(4-pyridylmethyl)-6-hydroxydecahydroisoquinoline; (4a,8a-cis)-6-(4-Fluorophenyl)-2-(pyridin-4-ylmethyl)perhydroisoquinolin-6-ol | Dexbrompheniramine Maleate |
| (4aalpha,8abeta)-2-Benzyl-6-(4-fluorophenyl)-6-hydroxydecahydroisoquinoline | Dexchlorpheniramine Maleate |
| (6aR,9R)-5-Bromo-7-methyl-N-(2-propynyl)-4,6,6a,7,8,9-hexahydroindolo[4,3-fg]quinoline-9-carboxamide | Dexfenfluramine HCl |
| (S)-(−)-N-(2-Amino-3-phenylpropyl)-2-(3,4-dichlorophenyl)-N-methylacetamide hydrochloride | Dicyclomine HCl |
| (S)-Methamphetamine HCl | Diethylpropion HCl |
| [1-(9-Ethyl-9H-Carbazol-3-Ylmethyl)-Pyrrolidin-3-Yl]-Carbamic Acid 1-(3-Benzyloxy-4-Methoxy-Benzyl)-Piperidin-3-Ylmethyl Ester | Dimethisoquin HCl |
| [1-(9-Ethyl-9H-Carbazol-3-Ylmethyl)-Pyrrolidin-3-Yl]-Carbamic Acid 2-(Tert-Butoxycarbonyl-Naphthalen-1-Ylmethyl-Amino)-Ethyl Ester | Dimetindene Maleate |
| [4-(4-Ethyl-3,5-Dimethyl-Pyrazol-1-Yl)-Phenyl]-[4-(3-Phenyl-Allyl)-Piperazin-1-Yl]-Methanone | Diphemanil Methylsulfate |
| 1-(1,2-Diphenylethyl)Piperidine Maleate, (+/−) | Diphenidol HCl |
| 1-(1,4-Ethano-1,2,3,4-tetrahydro-2-naphthylmethyl)-4-methylpiperazine hydrate; 1-(Benzobicyclo[2.2.2]octen-2-ylmethyl)-4-methylpiperazine hydrate | Diphenoxylate HCl |
| 1-(1-Adamantyl)-2-[4-(2H-naphtho[1,8-cd]isothiazol-2-ylmethyl)piperidin-1-yl]ethanone S,S-dioxide hydrochloride | Diphenylpyraline HCl |
| 1-(1-Naphthyl)Piperazine HCl | Dipropyldopamine HBr |
| 1-(2-Benzyloxyethyl)-4-(3-phenylpropyl)piperazine dihydrochloride | Doxepin HCl |
| 1-(2-Phenylethyl)piperidine oxalate | Dyclonine HCl |
| 1-(3-Chlorophenyl)Piperazine HCl | Ebastine |
| 1-(3-Chlorothien-2-yl)-2-[4-(4-fluorobenzyl)piperidin-1-yl]ethanol | Econazole Nitrate |
| 1-(4-Bromo-Benzenesulfonyl)-4-(2-Tert-Butylsulfanyl-Benzyl)-Piperazine | Epinastine HCl |
| 1-(4-Chloro-3-hydroxyphenyl)-2-[4-(4-fluorobenzyl)piperidin-1-yl]ethanol | Ethaverine HCl |
| 1-(4-Chlorophenyl)-3-(hexahydroazepin-1-ylmethyl)pyrrolidin-2-one | Ethopropazine HCl |
| 1-(4-Chlorophenyl)-3(R)-[4-(2-methoxyethyl)-1-piperazinylmethyl]pyrrolidin-2-one (−)-D-tartrate | Eticlopride HCl, S(−)- |
| 1-(4-Chlorophenyl)-3(R)-[4-(2-methoxyethyl)piperazin-1-ylmethyl]pyrrolidin-2-one dihydrochloride | Etofenamate |
| 1′-(4-Fluorobenzyl)-1,3-dihydrospiro[2-benzofuran-1,4′-piperidine] | Etonitazenyl Isothiocyanate |
| 1-(4-Fluorophenyl)-4-[4-(5-fluoro-2-pyrimidinyl)-1-piperazinyl]butan-1-ol hydrochloride | Femoxetine HCl |
| 1-(4-Fluorophenyl)-4-[4-(5-fluoropyrimidin-2-yl)piperazin-1-yl]butan-1-ol; 1-[4-(4-Fluorophenyl)-4-hydroxybutyl]-4-(5-fluoropyrimidin-2-yl)piperazine | Fenfluramine HCl |
| 1′-(4-Phenylbutyl)spiro[1,3-dihydroisobenzofuran-1,4′-piperidine] | Fenticonazole Nitrate |
| 1-(Cyclobutylmethyl)-2-[3-phenyl-2(E)-propenyl]pyrrolidine hydrochloride | Fipexide HCl |
| 1-(Cyclohexylmethyl)-3′-methoxy-5′-phenyl-4′,5′-dihydro-3′H-spiro[piperidine-4,1′-pyrano[4,3-c]pyrazole] | Flavoxate HCl |
| 1-(Cyclopropylmethyl)-4-[2-(4-fluorophenyl)-2-oxoethyl]piperidine hydrobromide | Flunarizine diHCl |
| 1,4-Bis[spiro[isobenzofuran-1(3H),4′-piperidin]-1′-yl]butane | Fluoxetine Related Compound B |
| 1-[(1R,3R)-2,2-Dimethyl-3-(2-phenoxyethyl)cyclobutylmethyl]piperidine | Fluperlapine |
| 1-[2-(3,4-Dichlorophenyl)ethyl]-3-(pyrrolidin-1-yl)piperidine | Fluphenazine Decanoate DiHCl |

TABLE 1-continued

| | |
|---|---|
| 1-[2-(3,4-Dichlorophenyl)ethyl]-4-(3-phenylpropyl)piperazine | Fluphenazine Enanthate DiHCl |
| 1-[2-(3,4-Dichlorophenyl)ethyl]-4-methylpiperazine | Fluphenazine HCl |
| 1-[2-(4-Fluorophenyl)ethyl]-4,4-dimethylhexahydroazepine hydrochloride | Fluphenazine N-Mustard DiHCl |
| 1-[2-[1-(3,4-Dichlorophenyl)-5-methyl-1H-1,2,4-triazol-3-ylsulfanyl]ethyl]piperidine oxalate | Flurazepam Related Compound C |
| 1-[2-Benzyloxy-1(R)-phenylethyl]-4-cyclohexylpiperazine dihydrochloride | Fluspirilene |
| 1-[3-(2-Oxo-3-phenylimidazolin-1-yl)propyl]spiro[piperidine-4,1'(3H)-isobenzofuran] hydrochloride; 1-Phenyl-3-[3-[spiro[piperidine-4,1'(3H)-isobenzofuran]-1-yl]propyl]imidazolin-2-one hydrochloride | GBR 12783 DiHCl |
| 1-[3-(3,4-Dimethoxyphenyl)propyl]-4-(4-phenylbutyl)perhydro-1,4-diazepine dihydrochloride | GBR 12909 DiHCl |
| 1-[3-(4-Chlorophenoxy)propyl]-4-methylpiperidine hydrochloride | GBR 13069 DiHCl |
| 1-[3-(4-Phenyl-2H-1,2,3-triazol-2-yl)propyl]piperidine | GBR-12935 DiHCl |
| 1-[4-(6-Methoxynaphthalen-1-yl)butyl]-3,3-dimethylpiperidine hydrochloride | GR 89696 Fumarate |
| 1-[4-[2-[1-(3,4-Dichlorophenyl)-1H-pyrazol-3-yloxy]ethyl]piperazin-1-yl]ethanone oxalate | Guanabenz Acetate |
| 11-[5-(4-Fluorophenyl)-5-oxopentyl]-5,6,7,8,9,10-hexahydro-7,10-iminocyclohept[b]indole | Guanadrel Sulfate |
| 1-Benzyl-3beta-[3-(cyclopropylmethoxy)propyl]-2alpha,3alpha,4beta-trimethylpiperidine | Halofantrine HCl |
| 1-Benzyl-3-methoxy-3',4'-dihydrospiro(piperidine-4,1'-thieno[3,2-c]pyrane) | HEAT HCl |
| 1'-Benzyl-3-methoxy-4-phenyl-3,4-dihydrospiro[furo[3,4-c]pyrazole-1,4'-piperidine] | Hexylcaine HCl |
| 1-Benzyl-4-(4-fluorophenoxymethyl)piperidine | Hycanthone |
| 1-Benzyl-4-[2-(4-fluorophenyl)-2-oxoethyl]piperidine maleate | Hydroxychloroquine Sulfate |
| 1-Benzyl-4-[3-phenyl-2(E)-propenyloxymethyl]piperidine hydrochloride | IBZM, S(−)- |
| 1-Benzyl-4-[4-(4-fluorophenyl)-3-cyclohexen-1-yl]piperazine dihydrochloride hemihydrate | ICI-199,441 HCl |
| 1'-Benzylspiro[1,2,3,4-tetrahydronaphthalene-1,4'-piperidine] | Ifenprodil Tartrate |
| 1'-Benzylspiro[indane-1,4'-piperidine] | Indatraline HCl |
| 1'-Butyl-3-Methoxy-4-phenyl-3,4-dihydrospiro[furo[3,4-c]pyrazole-1,4'-piperidine] | Iofetamine HCl |
| 1-Cyclohexyl-4-(3-phenoxypropyl)piperazine dihydrochloride | Isamoltane Hemifumarate |
| 1-Hydroxy-1'-(2-phenylethyl)spiro[1,2,3,4-tetrahydronaphthalene-2,4'-piperidine] hydrochloride | Isoxsuprine HCl |
| 1-Methyl-4-[2-(4-phenylpiperidin-1-yl)ethyl]-4,5,6,7-tetrahydro-1H-indazole oxalate | Ketotifen Fumarate Salt |
| 1-Phenyl-3-(1-propyl-1,2,5,6-tetrahydropyridin-3-yl)-1-propanone oxime oxalate | L-693,403 Maleate |
| 1-Phenyl-4-(pyrrolidin-1-ylmethyl)-1,4,6,7-tetrahydropyrano[4,3-c]pyrazole | L-741,626 |
| 2-(2-{[1-(3-Chloro-Benzyl)-Pyrrolidin-3-Yl]-Methyl-Carbamoyl}-2-Methyl-Propyl)-4,6-Dimethyl-Benzoic Acid | L-741,742 HCl |
| 2-(3,4-Dichlorophenyl)-N-methyl-N-[2-(1,2alpha,3alpha,4beta-tetramethylpiperidin-3beta-yl)ethyl]acetamide | L-745,870 TriHCl |
| 2-(Cyclohexylmethylaminomethyl)-8-methoxy-3,4-dihydro-2H-1-benzopyran hydrochloride | Levetimide HCl, R(−) |
| 2(S)-[(3aS,6aR)-5-Butyl-4-oxo-1,2,3,3a,4,6a-hexahydrocyclopenta[c]pyrrol-2-yl]propionic acid ethyl ester | Levobunolol HCl |
| 2-[2-[5-Methyl-1-(2-naphthyl)-1H-pyrazol-3-yloxy]ethylamino]ethanol hydrochloride | Lidoflazine |
| 2-[2-[N-(Cyclobutylmethyl)-N-methylamino]ethyl]-1,2,3,4-tetrahydronaphthalen-2-one | Lobeline HCl |

TABLE 1-continued

| | |
|---|---|
| 2-[3-[4-(2-Methoxyphenyl)piperazin-1-yl]propoxy]-9H-carbazole | Iomerizine diHCl |
| 2-[4-(4-Methoxybenzyl)piperazin-1-ylmethyl]-4H-1-benzopyran-4-one | Loxapine Succinate |
| 2-[N-[2-(3,4-Dichlorophenyl)ethyl]-N-methylaminomethyl]-1-ethylpyrrolidine | LY-53,857 Maleate |
| 2-Benzyl-3,4,8-trimethyl-2-azabicyclo[2.2.2]octane-6-carboxylic acid ethyl ester | Maprotiline HCl |
| 2-Butyl-2,3,4,4a,9,9a-hexahydro-1H-indeno[2,1-c]pyridine | Mazindol |
| 2-Chloro-11-(4-Methylpiperazino)Dibenz[B,F]Oxepin Maleate | MDL 12,330A HCl |
| 3-(1-Benzyl-2r,3c,4t-trimethylpiperidin-3t-yl)propionic acid ethyl ester hydrochloride | Mebhydroline 1,5-naphthalendisulfonate Salt |
| 3-(3-Chloro-4-cyclohexylphenyl)-1-(hexahydroazepin-1-yl)-1(Z)-propene hydrochloride; 1-[3-(3-Chloro-4-cyclohexylphenyl)-2(Z)-propenyl]hexahydroazepine hydrochloride | Meclizine HCl |
| 3-(4-Methylphenyl)-5-(1-propyl-1,2,5,6-tetrahydropyridin-3-yl)isoxazole oxalate | Mefloquine HCl |
| 3-(N-Benzyl-N-methylamino)-1-(4-nitrophenyl)piperidine | Meprylcaine HCl |
| 3,3'-Diethylthiacarbocyanine Iodide | Mesoridazine Besylate |
| 3-[1-(Benzocyclobutan-1-ylmethyl)piperidin-4-yl]-6-fluoro-1,2-benzisoxazole | Metaphit Methanesulfonate |
| 3-[2-(2-Adamantyl)ethyl]-3-azabicyclo[3.2.2]nonene | Metaphit |
| 3-[3-(4-Methylphenyl)isoxazol-5-yl]-1-propyl-1,2,5,6-tetrahydropyridine | Methantheline Bromide |
| 3a,6-Epoxy-2-[2-(4-fluorophenyl)ethyl]-2,3,3a,6,7,7a-hexahydro-1H-isoindole | Methdilazine |
| 3a,6-Epoxy-2-[2-(4-fluorophenyl)ethyl]perhydroisoindole | Methiothepin Mesylate |
| 3-Mercapto-2-Methylpropanoic Acid 1,2-Diphenylethylamine Salt | Methixene HCl |
| 3-Phenyl-1-(1-propyl-1,2,5,6-tetrahydro-3-pyridyl)-1-propanone oxime monohydrochloride | Methylene Violet 3Rax HCl |
| 3-Quinuclidinyl Benzilate | Metipranolol |
| 3-Tropanyl-3,5-Dichlorobenzoate | Mianserin HCl |
| 3-Tropanyl-Indole-3-Carboxylate HCl | Miconazole |
| 4-(1H-Indol-4-Yl)-Piperazine-1-Carboxylic Acid 2-(5-Bromo-2-Ethoxy-Phenylamino)-Cyclohexylmethyl Ester | ML-9 HCl |
| 4-(2-Tert-Butylsulfanyl-Benzyl)-Piperazine-1-Carboxylic Acid 2-Thiophen-2-Yl-Ethyl Ester | Morantel Hydrogen L-Tartrate |
| 4-(3,5-Dimethoxy-Phenyl)-Piperazine-1-Carboxylic Acid 1-(2-Fluoro-Benzyl)-Piperidin-2-Ylmethyl Ester | MR 16728 HCl |
| 4-(3-Nitro-5-Sulfamoyl-Thiophen-2-Yl)-Piperazine-1-Carboxylic Acid 1-(2-Fluoro-5-Methoxy-Benzyl)-Piperidin-3-Ylmethyl Ester | MT-210 |
| 4-(4-Benzylpiperazin-1-ylmethyl)-7-methoxy-2H-1-benzopyran-2-one | N-(2-Adamantyl)-N-[2-(2-adamantyl)ethyl]-N-methylamine hydrochloride |
| 4-(4-Bromophenyl)-5-[2-(dihexylamino)ethyl]thiazol-2-amine dihydrochloride | N-[1-(2-Indanyl)piperidin-4-yl]-N-methylcarbamic acid isobutyl ester fumarate |
| 4-(4-Fluorobenzoyl)-1-(4-Phenylbutyl)Piperidine Oxalate | N-[1-[4-Methoxy-3-(2-phenylethoxy)benzyl]-4-methylpentyl]-N-propylamine |
| 4-(4-Methylphenyl)-1-(3-morpholinopropyl)-1,2,3,6-tetrahydropyridine | N-[2-(3,4-Dichlorophenyl)ethyl]-N-ethyl-N-[2-(1-pyrrolidinyl)ethyl]amine |
| 4-(5-Trifluoromethyl-Pyridin-2-Yl)-Piperazine-1-Carboxylic Acid Pent-2-Ynyl Ester | N-[2-(3,4-Dichlorophenyl)ethyl]-N-methyl-N-(2-pyrrolidinoethyl)amine dihydrobromide |
| 4-(Dimethylamino)-1-phenylcyclohexanol | N-[4-[4-(Diethylamino)piperidin-1-yl]phenyl]methanesulfonamide |
| 4,7-Epoxy-2-[2-(4-fluorophenyl)ethyl]-2,3,3a,4,7,7a-hexahydro-1H-isoindole | N1-(1-Adamantyl)-N2-(2-methylphenyl)acetamidine |
| 4-[1-(3-[18F]fluoropropyl)piperidin-4-ylmethoxy]benzonitrile | N1-[2-(3,4-Dichlorophenyl)ethyl]-N1,N2,N2-trimethyl-1,2-ethanediamine |
| 4-[1-(4-Chlorobenzyl)-4-(benzylpiperidin-4-yl]-2-hydroxy-4-oxobut-2-enoic acid | Nafronyl Oxalate Salt |
| 4-[1-(4-Fluorophenyl)-1-hydroxymethyl]-1-[3-(4-fluorophenoxy)propyl]piperidine | Naftifine |
| 4-[2-(Dipropylamino)ethyl]-2-(2-phenylethoxy)anisole hydrochloride | Naftopidil diHCl |
| 4-[2-(Dipropylamino)ethyl]-5,8-dimethylcarbazole hydrochloride | Naltriben Mesylate |

TABLE 1-continued

| | |
|---|---|
| 4-[2-[1-(3,4-Dichlorophenyl)-5-methyl-1H-pyrazol-3-yloxy]ethyl]morpholine | NE-100 |
| 4-[2-[1-(Cyclopropylmethyl)piperidin-4-yl]acetyl]benzonitrile fumarate | Nefazodone |
| 4-[4-(N-Benzyl-N-methylamino)piperidin-1-yl]benzonitrile | N-Ethyl-N-[2-(1-piperidinyl)ethyl]-N-[2-[4-(trifluoromethoxy)phenyl]ethyl]amine |
| 4-[N-[2-[N'-(4-Fluorobenzyl)-N'-methylamino]ethyl]-N-methylamino]-1-(4-fluorophenyl)-1-butanone dihydrochloride | Nicergoline |
| 4-Benzyl-1-[4-(4-fluorophenyl)-4-hydroxybutyl]piperidine hydrochloride | Niguldipine HCl, (+/−)- |
| 4-Bromo-N-[1-(9-Ethyl-9H-Carbazol-3-Ylmethyl)-Pyrrolidin-3-Yl]-2-Trifluoromethoxy-Benzenesulfonamide | Nisoxetine HCl |
| 4'-Chloro-3-Alpha-(Diphenylmethoxy)Tropane HCl | NP-07 |
| 4-Furan-2-Ylmethyl-Piperazine-1-Carboxylic Acid 2-{4-[3-(2-Trifluoromethyl-Phenothiazin-10-Yl)-Propyl]-Piperazin-1-Yl}-Ethyl Ester | Nylidrin HCl |
| 4-Methoxy-1-[2-(4-phenylpiperazin-1-yl)ethyl]-6H-dibenzo[b,d]pyran hydrochloride | Octoclothepin Maleate, (±)- |
| 4-Methoxy-N-[1-(7-Methoxy-Benzo[1,3]Dioxol-5-Ylmethyl)-Pyrrolidin-3-Yl]-Benzenesulfonamide | Oxamniquine |
| 4-Phenyl-1-(3-phenylpropyl)-4-(pyrrolidin-1-ylcarbonyl)piperidine | Oxamniquine Related Compound A |
| 5-(2-Pyrrolidinoethyl)-4-(2,4,6-trimethoxyphenyl)thiazole-2-amine dihydrochloride | Oxamniquine Related Compound B |
| 5-(N-Ethyl-N-Isopropyl)-Amiloride | Oxatomide |
| 6-[1-Hydroxy-2-[4-(2-phenylethyl)piperidin-1-yl]ethyl]-1,2,3,4-tetrahydroquinolin-2-one | Oxiconazole Nitrate |
| 6-[2-(4-Benzylpiperidin-1-yl)ethyl]-3-methylbenzothiazol-2(3H)-one | Panamesine hydrochloride |
| 6-[2-[4-(2-Phenylethyl)piperidin-1-yl]ethyl]-1,2,3,4-tetrahydroquinolin-2-one | Panaxatriol |
| 6-[3-(Morpholin-4-yl)propyl]benzothiazol-2(3H)-one | PAPP |
| 6-[6-(4-Hydroxypiperidin-1-yl)hexyloxy]-3-methyl-2-phenyl-4H-1-benzopyran-4-one | Paroxetine |
| 7-(4-Methoxyphenyl)-4-[4-(4-pyridyl)butyl]hexahydro-1,4-thiazepine | Paxilline |
| 7-[3-[4-(4-Fluorobenzoyl)piperidin-1-yl]propoxy]-4H-1-benzopyran-4-one hydrochloride | p-Chlorobenzhydrylpiperazine |
| 9-[4-({[4'-(trifluoromethyl)-1,1'-biphenyl-2-yl]carbonyl}amino)piperidin-1-yl]-N-(2,2,2-trifluoroethyl)-9H-fluorene-9-carboxamide | Penbutolol Sulfate |
| 9-Hydroxy-2,3,6,7,7a,8,12b,12c-octahydro-1H,5H-naphtho[1,2,3-ij]quinolizine | Pentamidine Isethionate |
| Acetophenazine Maleate | Pergolide Methanesulfonate |
| Acrinol | Perospirone |
| Ajmaline | Phenamil Methanesulfonate |
| Alaproclate HCl | Phenosafranin HCl |
| Aloe-Emodin | Piboserod |
| Alprenolol D-Tartrate Salt Hydrate | Pimozide |
| Alprenolol HCl | Pinacyanol Chloride |
| AMI-193 | Pindobind, (+/−)- |
| Aminobenztropine | Piperacetazine |
| Amiodarone HCl | Piperidolate HCl |
| Amodiaquine HCl | Pirenperone |
| Amorolfine HCl | PPHT HCl, (±)- |
| Amoxapine | Prenylamine Lactate Salt |
| AN2/AVex-73; AE-37; ANAVEX 2-73; N-(2,2-Diphenyltetrahydrofuran-3-ylmethyl)-N,N-dimethylamine | Pridinol Methanesulfonate Salt |
| Anavex 1-41; AE-14; N-(5,5-Diphenyltetrahydrofuran-3-ylmethyl)-N,N-dimethylamine hydrochloride | Procyclidine HCl |
| Anavex 19-144; AE-37met: AN19/AVex-144 | Proflavine Hemisulfate Salt |
| Anavex 7-1037 | Propafenone HCl |
| Anisotropine Methylbromide | Proparacaine HCl |
| Anpirtoline | Propiomazine |
| ARC 239 DiHCl | Protokylol |
| Auramine O HCl | Protriptyline HCl |
| Azaperone | Pyrilamine Maleate |
| Azatadine Maleate | Pyrimethamine |
| Azelastine HCl | Pyrrolidine-1,2-Dicarboxylic Acid 1-[1-(4-Allyloxy-Benzyl)-Piperidin-2-Ylmethyl] Ester 2-Benzyl Ester |

TABLE 1-continued

| | |
|---|---|
| Bamethan sulfate | Pyrvinium Pamoate |
| BD 1008 DiHBr | Quetiapine Fumarate |
| BD-1063 | Quinacrine HCl |
| Benextramine TetraHCl | Quinaldine Red |
| Benfluorex HCl | Quipazine Dimaleate |
| Benidipine HCl | Quipazine, 6-Nitro-, Maleate |
| Benoxathian HCl | Raloxifene |
| Benproperine Phosphate | Rimantadine HCl |
| Benzododecinium bromide | Rimcazole hydrochloride |
| Benzphetamine HCl | Risperidone |
| Benztropine Mesylate | Ritanserin |
| Bephenium Hydroxynaphthoate | Ritodrine HCl |
| Bepridil HCl | RS 23597-190 HCl |
| Berberine chloride | RS 67333 HCl |
| Betaxolol HCl | RS 67506 HCl |
| Bifemelane | Safranin O HCl |
| BMY 7378 DiHCl | Salmeterol |
| Bopindolol Malonate | SB203186 |
| BP 554 Maleate | SCH-23390 HCl, R(+)- |
| Bromhexine HCl | Sertaconazole Nitrate |
| Bromodiphenhydramine HCl | Sertindole |
| Bromperidol | Sertraline |
| Brompheniramine Maleate | Sibutramine HCl |
| BTCP HCl | Siramesine hydrochloride |
| Buclizine HCl | SKF-525A HCl |
| Buflomedil HCl | SKF-96365 HCl |
| Bupropion HCl | SNC 121 |
| Buspirone HCl | Spiperone HCl |
| Butacaine Sulfate | T-226296 |
| Butaclamol HCl, (±)- | Tegaserod Maleate |
| Butenafine HCl | Terbinafine HCl |
| Butoconazole Nitrate | Terconazole |
| BW 723C86 HCl | Terfenadine |
| Carbetapentane Citrate | Terfenadine Related Compound A |
| Carbinoxamine Maleate | Tetrindole Mesylate |
| Carpipramine DiHCl DiH2O | Thiethylperazine Malate |
| Carvedilol | Thioperamide Maleate |
| Cephapirin Benzathine | Thioproperazine |
| CGS-12066A Maleate | Thioridazine |
| Chloroprocaine HCl | Thiothixene |
| Chlorpheniramine Maleate | Thiothixene, (E)- |
| Chlorphenoxamine HCl | Thonzonium Bromide |
| Chlorprothixene | Tioconazole Related Compound A |
| Cinanserin HCl | TMB-8 HCl |
| Cinnarizine | Tolterodine L-Tartrate |
| Cirazoline HCl | Toremifene Citrate |
| Cis-(+/−)-N-Methyl-N-[2-(3,4-Dichlorophenyl)Ethyl]-2-(1-Pyrrolidinyl)Cyclohexamine DiHBr | Tramazoline HCl |
| Cis(Z)-Flupentixol DiHCl | Trans-U-50488 Methanesulfonate, (±)- |
| cis-2-(Cyclopropylmethyl)-7-(4-fluorobenzoyl)perhydropyrido[1,2-a]pyrazine | Tridihexethyl Chloride |
| cis-2-[4-(Trifluoromethyl)benzyl]-3a,4,7,7a-tetrahydroisoindoline | Trifluoperazine HCl |
| Cisapride Hydrate | Trifluperidol HCl |
| Citalopram HBr | Trihexyphenidyl HCl |
| Clemastine Fumarate | Trimeprazine Hemi-L-Tartrate |
| Clemizole HCl | Trimipramine Maleate |
| Clenbuterol HCl | Tripelennamine HCl |
| Clidinium Bromide | Triprolidine HCl |
| Clobenpropit 2HBr | Triprolidine HCl Z Isomer |
| Clofazimine | Tropanyl 3,5-Dimethylbenzoate |
| Clofilium Tosylate | Tropine 2-(4-Chlorophenoxy)Butanoate, Maleate |
| Clomiphene Citrate | U-50488 HCl, (−)- |
| Clomiphene Related Compound A | U-62066 |
| Clomipramine | UH 232 Maleate, (+)- |
| Cloperastine HCl | Vesamicol HCl |
| Clorgyline HCl | Vinpocetine |
| Clozapine | W-7 HCl |
| Conessine | WB-4101 HCl |

Preferably, the table above includes also reduced haloperidol. Reduced haloperidol is an active metabolite of haloperidol that is produced in humans, shows a high affinity (in the low nanomolar range) for sigma-1 receptors, and produces an irreversible blockade of sigma-1 receptors both in experimental animals and human cells.

Examples of well known methods of producing a prodrug of a given acting compound are known to those skilled in the art (e.g. in Krogsgaard-Larsen et al., Textbook of Drug design and Discovery, Taylor & Francis (April 2002)).

In a preferred embodiment, the sigma ligand in the context of the present invention has the general formula (I) as depicted above.

In a preferred embodiment, $R_1$ in the compounds of formula (I) is selected from H, —$COR_8$, and substituted or unsubstituted alkyl. More preferably, $R_1$ is selected from H, methyl and acetyl. A more preferred embodiment is when $R_1$ is H.

In another preferred embodiment, $R_2$ in the compounds of formula (I) represents H or alkyl, more preferably methyl.

In yet another preferred embodiment of the invention, $R_3$ and $R_4$ in the compounds of formula (I) are situated in the meta and para positions of the phenyl group, and preferably, they are selected independently from halogen and substituted or unsubstituted alkyl.

In an especially preferred embodiment of the invention, in the compounds of formula (I) both $R_3$ and $R_4$ together with the phenyl group form an optionally substituted fused ring system (for example, a substituted or unsubstituted aryl group or a substituted or unsubstituted, aromatic or non-aromatic heterocyclyl group may be fused), more preferably, a naphthyl ring system.

Also in the compounds of formula (I), embodiments where n is selected from 2, 3, 4 are preferred in the context of the present invention, more preferably n is 2.

Finally, in another embodiment it is preferred in the compounds of formula (I) that $R_5$ and $R_6$ are, each independently, $C_{1-6}$alkyl, or together with the nitrogen atom to which they are attached form a substituted or unsubstituted heterocyclyl group a, in particular a group chosen among morpholinyl, piperidinyl, and pyrrolidinyl group. More preferably, $R_5$ and $R_6$ together form a morpholine-4-yl group.

In preferred variants of the invention, the sigma ligand of formula (I) is selected from:

[1] 4-{2-(1-(3,4-dichlorophenyl)-5-methyl-1H pyrazol-3-yloxy)ethyl}morpholine
[2] 2-[1-(3,4-Dichlorophenyl)-5-methyl-1H-pyrazol-3-yloxy]-N,N-diethylethanamine
[3] 1-(3,4-Dichlorophenyl)-5-methyl-3-[2-(pyrrolidin-1-yl)ethoxy]-1H-pyrazole
[4] 1-(3,4-Dichlorophenyl)-5-methyl-3-[3-(pyrrolidin-1-yl)propoxy]-1H-pyrazole
[5] 1-{2-[1-(3,4-Dichlorophenyl)-5-methyl-1H-pyrazol-3-yloxy]ethyl}piperidine
[6] 1-{2-[1-(3,4-dichlorophenyl)-5-methyl-1H-pyrazol-3-yloxy]ethyl}-1H-imidazole
[7] 3-{1-[2-(1-(3,4-Dichlorophenyl)-5-methyl-1H-pyrazol-3-yloxy)ethyl]piperidin-4-yl}-3H-imidazo[4,5-b]pyridine
[8] 1-{2-[1-(3,4-Dichlorophenyl)-5-methyl-1H-pyrazol-3-yloxy]ethyl}-4-methylpiperazine
[9] Ethyl 4-{2-[1-(3,4-dichlorophenyl)-5-methyl-1H-pyrazol-3-yloxy]ethyl}piperazine carboxylate
[10] 1-(4-(2-(1-(3,4-dichlorophenyl)-5-methyl-1H-pyrazol-3-yloxy)ethyl)piperazin-1-yl)ethanone
[11] 4-{2-[1-(4-Methoxyphenyl)-5-methyl-1H-pyrazol-3-yloxy]ethyl}morpholine
[12] 1-(4-Methoxyphenyl)-5-methyl-3-[2-(pyrrolidin-1-yl)ethoxy]-1H-pyrazole
[13] 1-(4-Methoxyphenyl)-5-methyl-3-[3-(pyrrolidin-1-yl)propoxy]-1H-pyrazole
[14] 1-[2-(1-(4-Methoxyphenyl)-5-methyl-1H-pyrazol-3-yloxy)ethyl]piperidine
[15] 1-{2-[1-(4-Methoxyphenyl)-5-methyl-1H-pyrazol-3-yloxy]ethyl}-1H-imidazole
[16] 4-{2-[1-(3,4-Dichlorophenyl)-5-phenyl-1H-pyrazol-3-yloxy]ethyl}morpholine
[17] 1-(3,4-Dichlorophenyl)-5-phenyl-3-[2-(pyrrolidin-1-yl)ethoxy]-1H-pyrazole
[18] 1-(3,4-Dichlorophenyl)-5-phenyl-3-[3-(pyrrolidin-1-yl)propoxy]-1H-pyrazole
[19] 1-{2-[1-(3,4-Dichlorophenyl)-5-phenyl-1H-pyrazol-3-yloxy]ethyl}piperidine
[20] 1-{2-[1-(3,4-Dichlorophenyl)-5-phenyl-1H-pyrazol-3-yloxy]ethyl}-1H-imidazole
[21] 2-{2-[1-(3,4-dichlorophenyl)-5-phenyl-1H-pyrazol-3-yloxy]ethyl}-1,2,3,4-tetrahydroisoquinoline
[22] 4-{4-[1-(3,4-Dichlorophenyl)-5-methyl-1H-pyrazol-3-yloxy]butyl}morpholine
[23] 1-(3,4-Dichlorophenyl)-5-methyl-3-[4-(pyrrolidin-1-yl)butoxy]-1H-pyrazole
[24] 1-{4-[1-(3,4-Dichlorophenyl)-5-methyl-1H-pyrazol-3-yloxy]butyl}piperidine
[25] 1-{4-[1-(3,4-Dichlorophenyl)-5-methyl-1H-pyrazol-3-yloxy]butyl}-4-methylpiperazine
[26] 1-{4-[1-(3,4-Dichlorophenyl)-5-methyl-1H-pyrazol-3-yloxy]butyl}-1H-imidazole
[27] 4-[1-(3,4-Dichlorophenyl)-5-methyl-1H-pyrazol-3-yloxy]-N,N-diethylbutan-1-amine
[28] 1-{4-[1-(3,4-dichlorophenyl)-5-methyl-1H-pyrazol-3-yloxy]butyl}-4-phenylpiperidine
[29] 1-{4-[1-(3,4-dichlorophenyl)-5-methyl-1H-pyrazol-3-yloxy]butyl}-6,7-dihydro-1H-indol-4(5H)-one
[30] 2-{4-[1-(3,4-dichlorophenyl)-5-methyl-1H-pyrazol-3-yloxy]butyl}-1,2,3,4-tetrahydroisoquinoline
[31] 4-{2-[1-(3,4-dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]-N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-Dichlorophenyl)-5-isopropyl-1H-pyrazol-3-yloxy]ethyl}-1,2,3,4-tetrahydroisoquinoline
[37] 4-{2-[1-(3,4-dichlorophenyl)-1H-pyrazol-3-yloxy]ethyl}morpholine
[38] 2-[1-(3,4-dichlorophenyl)-1H-pyrazol-3-yloxy] N,N-diethylethanamine
[39] 1-(3,4-dichlorophenyl)-3-[2-(pyrrolidin-1-yl)ethoxy]-1H-pyrazole
[40] 1-{2-[1-(3,4-dichlorophenyl)-1H-pyrazol-3-yloxy]ethyl}piperidine
[41] 1-(3,4-dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1 (3,4-Dichlorophenyl)-4,5-dimethyl-1H-pyrazol-3-yloxy]ethyl}morpholine

[46] 2-[1-(3,4-Dichlorophenyl)-4,5-dimethyl-1H-pyrazol-3-yloxy]-N,N-diethylethanamine
[47] 1-(3,4-Dichlorophenyl)-4,5-dimethyl-3-[2-(pyrrolidin-1-yl)ethoxy]-1H-pyrazole
[48] 1-(3,4-Dichlorophenyl)-4,5-dimethyl-3-[3-(pyrrolidin-1-yl)propoxy]-1H-pyrazole
[49] 1-{2-[1-(3,4-Dichlorophenyl)-4,5-dimethyl-1H-pyrazol-3-yloxy]ethyl}piperidine
[50] 4-{4-[1-(3,4-dichlorophenyl)-1H-pyrazol-3-yloxy]butyl}morpholine
[51] (2S,6R)-4-{4-[1-(3,4-dichlorophenyl)-1H-pyrazol-3-yloxy]butyl}-2,6-dimethylmorpholine
[52] 1-{4-[1-(3,4-Dichlorophenyl)-1H-pyrazol-3-yloxy]butyl}piperidine
[53] 1-(3,4-Dichlorophenyl)-3-[4-(pyrrolidin-1-yl)butoxy]-1H-pyrazole
[55] 4-[1-(3,4-dichlorophenyl)-1H-pyrazol-3-yloxy]-N,N-diethylbutan-1-amine
[56] N-benzyl-4-[1-(3,4-dichlorophenyl)-1H-pyrazol-3-yloxy]-N-methylbutan-1-amine
[57] 4-[1-(3,4-dichlorophenyl)-1H-pyrazol-3-yloxy]-N-(2-methoxyethyl)-N-methylbutan-1-amine
[58] 4-{4-[1-(3,4-dichlorophenyl)-1H-pyrazol-3-yloxy]butyl}thiomorpholine
[59] 1-[1-(3,4-Dichlorophenyl)-5-methyl-3-(2-morpholinoethoxy)-1H-pyrazol-4-yl]ethanone
[60] 1-{1-(3,4-dichlorophenyl)-5-methyl-3-[2-(pyrrolidin-1-yl)ethoxy]-1H-pyrazol-4-yl}ethanone
[61] 1-{1-(3,4-dichlorophenyl)-5-methyl-3-[2-(piperidin-1-yl)ethoxy]-1H-pyrazol-4-yl}ethanone
[62] 1-{1-(3,4-dichlorophenyl)-3-[2-(diethylamino)ethoxy]-5-methyl-1H-pyrazol-4-yl}ethanone
[63] 4-{2-[5-Methyl-1-(naphthalen-2-yl)-1H-pyrazol-3-yloxy]ethyl}morpholine
[64] N,N-Diethyl-2-[5-methyl-1-(naphthalen-2-yl)-1H-pyrazol-3-yloxy]ethanamine
[65] 1-{2-[5-Methyl-1-(naphthalen-2-yl)-1H-pyrazol-3-yloxy]ethyl}piperidine
[66] 5-Methyl-1-(naphthalen-2-yl)-3-[2-(pyrrolidin-1-yl)ethoxy]-1H-pyrazole or their pharmaceutically acceptable salts, isomers, prodrugs or solvates.

In a more preferred variant of the invention, the sigma ligand of formula (I) is 4-{2-[5-Methyl-1-(naphthalen-2-yl)-1H-pyrazol-3-yloxy]ethyl}morpholine. This particular compound is designated in the examples of the present invention as compound 63.

The compounds of formula (I) and their salts or solvates can be prepared as disclosed in the previous application WO2006/021462.

In another preferred embodiment, the sigma ligand in the context of the present invention has the general formula (II) as depicted above.

In another embodiment of the invention, it is preferred that in the compound of formula (II), at least one of $R_1$ to $R_3$ is hydrogen. In another embodiment of the invention, it is preferred that in the compound of formula (II), at least one of $R_1$ to $R_3$ is halogen. In another embodiment, it is preferred that two of $R_1$ to $R_3$ are hydrogen or halogen, the last being preferably chloride.

In another embodiment, $R_4$ in the compounds of formula (II) is preferably a lower alkyl, more preferably is methyl.

In one embodiment in the compounds of formula (II) $R_5$ and $R_6$ are independently an alkyl, more preferably a $C_1$-$C_5$ alkyl, even more preferably ethyl or isopropyl.

In another embodiment in the compounds of formula (II) $R_5$ and $R_6$ form, together with the nitrogen to which they are attached, a substituted or unsubstituted heterocyclyl group, preferably selected from pyrrolidine, piperidine, azepane and morpholine.

Further, in a preferred embodiment in the compounds of formula (II) n is 1, 2, 3, 4 or 5. Preferred compounds of formula (II) are the following:
[67] 4-[2-(3,4-dichlorophenyl)-5-methyl-1H-1,2,4-triazole-3-ylthioethyl]morpholine;
[68] 1-[2-(3,4-dichlorophenyl)-5-methyl-1H-1,2,4-triazole-3-yl-thioethyl]piperidine;
[69] 1-[2-(3,4-dichlorophenyl)-5-methyl-1H-1,2,4-triazole-3-yl-thioethyl]pyrrolidine;
[70] 2-[2-(3,4-dichlorophenyl)-5-methyl-1H-1,2,4-triazole-3-yl-thio]-N,N-diisopropyl ethanamine;
[71] 2-[1-(3,4-dichlorophenyl)-5-methyl-1H-1,2,4-triazole-3-yl-thio]-N,N-diethyl ethanamine;
[72] 1-[2-(1-(3,4-dichlorophenyl)-5-methyl-1H-1,2,4-triazol-3-yl-thio)ethyl]azepane;
[73] 4-[3-(1-(3,4-dichlorophenyl)-5-methyl-1H-1,2,4-triazol-3-ylthio)propyl]morpholine;
[74] 1-[3-(1-(3,4-dichlorophenyl)-5-methyl-1H-1,2,4-triazol-3-yl-thio)propyl]-4-pyrrolidine;
[75] 1-[3-(1-(3,4-dichlorophenyl)-5-methyl-1H-1,2,4-triazol-3-ylthio)propyl]-4-phenylpiperidine;
[76] 1-[4-(1-(3,4-dichlorophenyl)-5-methyl-1H-1,2,4-triazol-3-yl-thio)butyl]-4-phenylpiperidine;
[77] 4-[4-(1-(3,4-dichlorophenyl)-5-methyl-1H-1,2,4-triazol-3-yl-thio)butyl]morpholine;
[78] 1-[5-(1-(3,4-dichlorophenyl)-5-methyl-1H-1,2,4-triazol-3-ylthio)pentyl]piperidine;
[79] 4-[5-(1-(3,4-dichlorophenyl)-5-methyl-1H-1,2,4-triazol-3-ylthio)pentyl]morpholine;
[80] 1-[5-(1-(3,4-dichlorophenyl)-5-methyl-1H-1,2,4-triazol-3-ylthio)pentyl]pyrrolidine;
[81] 1-[2-(1-(3,4-dichlorophenyl)-5-methyl-1H-1,2,4-(ri-azol-3-yl-sulfinyl)ethyl]pyrrolidine;
[82] 4-[2-(1-(3,4-dichlorophenyl)-5-methyl-1H-1,2,4-triazol-3-yl-sulfinyl)-ethyl]-morpholine;
[83] 2-[2-(1-(3,4-dichlorophenyl)-5-methyl-1H-1,2,4-triazol-3-ylsulfinyl]-N,N-diisopropylethanamine;
[84] 1-[4-(1-(3,4-dichlorophenyl)-5-methyl-1H-1,2,4-triazol-3-ylsulfinyl)butyl]-4-phenylpiperidine;
[85] 1-[2-(3,4-dichlorophenyl)-5-methyl-1H-1,2,4-triazol-3-ylsulfonyl]ethylpyrrolidine;
[86] 2-[1-(3,4-dichlorophenyl)-5-methyl-1H-1,2,4-triazol-3-yl-sulfonyl]-N,N-diethylethanamine;
[87] 4-[4-(1-(3,4-dichlorophenyl)-5-methyl-1H-1,2,4-triazol-3-yl-sulfonyl)-butyl]morpholine;
[88] 1-[2-(3,4-dichlorophenyl)-5-methyl-1H-1,2,4-triazol-3-yloxy)ethyl]piperidine;
[89] 2-[1-(3,4-dichlorophenyl)-5-methyl-1H-1,2,4-triazol-3-yloxy]-N,N-diethylethanamine;
[90] 1-[2-(1-(3,4-dichlorophenyl)-5-methyl-1H-1,2,4-triazol-3-yloxy)ethyl]pyrrolidine;
[91] 4-[2-(1-(3,4-dichlorophenyl)-5-methyl-1H-1,2,4-triazol-3-yloxy)ethyl]morpholine;
[92] 2-(5-methyl-1-phenyl-1H-1,2,4-triazol-3-yloxy)-N,N-diethylethanamine;
[93] 1-[2-(5-methyl-1-phenyl-1H-1,2,4-triazol-3-yloxy)ethyl]pyrrolidine;
[94] 4-[2-(5-ethyl-1-phenyl-1H-1,2,4-triazol-3-yloxy)ethyl]morpholine;
[95] 1-[2-(5-methyl-1-phenyl-1H-1,2,4-triazol-3-yloxy)ethyl]piperidine;
[96] 4-[4-(5-methyl-1-phenyl-1H-1,2,4-triazol-3-yloxy)butyl]morpholine;

[97] 1-[2-(1-(3,4-dichlorophenyl)-5-methyl-1H-1,2,4-triazol-3-ylthio)ethyl]-4-methylpiperidine;
[98] 4-[2-(5-methyl-1-phenyl-1H-1,2,4-triazol-3-ylthio)ethyl]morpholine;
[99] 4-[2-(1-(4-chlorophenyl)-5-methyl-1H-1,2,4-triazol-3-ylthio)ethyl]morpholine;
[100] N-[2-(1-(3-chlorophenyl)-5-methyl-1H-1,2,4-triazol-3-ylthio)ethyl]-N,N-diisopropylpropan-2-amine;
[101] 1-[2-(1-(3-chlorophenyl)-5-methyl-1H-1,2,4-triazol-3-ylthio)ethyl]piperidine;
[102] 4-[2-(1-(3-chlorophenyl)-5-ethyl-1H-1,2,4-triazol-3-ylthio)ethyl]morpholine;
[103] 4-[2-(1-(3-chlorophenyl)-5-methyl-1H-1,2,4-triazol-3-ylthio)ethyl]pyrrolidine;
[104] 2-[1-(3-chlorophenyl)-5-methyl-1H-1,2,4-triazol-3-ylthio]-N,N-diethylethanamine;
[105] 4-[1-(3,4-dichlorophenyl)-5-methyl-1H-1,2,4-triazol-3-ylthio]-N,N-diethylbutan-1-amine;
[106] 1-[4-(1-(3,4-dichlorophenyl)-5-methyl-1H-1,2,4-triazol-3-ylthio)butyl]piperidine;
[107] 1-[4-(1-(3,4-dichlorophenyl)-5-methyl-1H-1,2,4-triazol-3-ylthio)butyl]pyrrolidine;
[108] 2-[1-(3,4-dichlorophenyl)-5-methyl-1H-1,2,4-triazol-3-ylsulfinyl]-N,N-diethylethanamine;
[109] 1-[2-(1-(3-chlorophenyl)-5-methyl-1H-1,2,4-triazol-3-yl-sulfinyl)ethyl]pyrrolidine
[110] 1-[2-(1-(3-chlorophenyl)-5-methyl-1H-1,2,4-triazol-3-yl-sulfinyl)ethyl]morpholine
[111] 1-[2-(1-(3-chlorophenyl)-5-methyl-1H-1,2,4-triazol-3-yl-sulfinyl)ethyl]-N,N-diethylamine;
[112] 1-[2-(1-(3-chlorophenyl)-5-methyl-1H-1,2,4-triazol-3-yl-sulfonyl)ethyl]pyrrolidine
[113] 1-[2-(1-(3-chlorophenyl)-5-methyl-1H-1,2,4-triazol-3-yl-sulfonyl)ethyl]-N,N-diisopropilamine;
[114] 1-[2-(1-(3-chlorophenyl)-5-methyl-1H-1,2,4-triazol-3-yl-sulfonyl)ethyl]-N,N-diethylamine;

or a pharmaceutically acceptable salt, isomer, prodrug or solvate thereof.

Additionally, in another preferred embodiment of the invention the compound of formula (II) is an oxalic salt thereof.

Preferred salts of the compounds of formula II are the following:

[115] 4-[2-(3,4-dichlorophenyl)-5-methyl-1H-1,2,4-triazole-3-ylthio ethyl]morpholine oxalate;
[116] 1-[2-(3,4-dichlorophenyl)-5-methyl-1H-1.2.4-triazole-3-yl-thio)ethyl]piperidine oxalate;
[117] 1-[2-(3,4-dichlorophenyl)-5-methyl-1H-1,2,4-triazole-3-yl-thio ethyl]pyrrolidine oxalate;
[118] 2-[2-(3,4-dichlorophenyl)-1-methyl-1H-1,2,4-triazole-3-yl-thio]-N,N-diisopropyl ethanamine oxalate;
[119] 2-[1-(3,4-dichlorophenyl)-5-methyl-1H-1,2,4-triazole-3-yl-thio]-N,N-diethyl ethanamine oxalate;
[120] 1-[2-(1-(3,4-dichlorophenyl)-5-methyl-1H-1,2,4-triazol-3-yl-thio)ethyl]azepane oxalate;
[121] 4-[3-(1-(3,4-dichlorophenyl)-5-methyl-1H-1,2,4-triazol-3-ylthio)propyl]morpholine oxalate;
[122] 1-[3-(1-(3,4-dichlorophenyl)-5-methyl-1H-1,2,4-triazol-3-yl-thio)propyl]pyrrolidine oxalate;
[123] 1-[3-(1-(3,4-dichlorophenyl)-5-methyl-1H-1,2,4-triazol-3-ylthio)propyl]-4-phenylpiperidine oxalate;
[124] 1-[4-(1-(3,4-dichlorophenyl)-5-methyl-1H-1,2,4-triazol-3-yl-thio)butyl]-4-phenylpiperidine oxalate;
[125] 4-[4-(1-(3,4-dichlorophenyl)-5-methyl-1H-1,2,4-triazol-3-yl-thio)butyl]morpholine oxalate;
[126] 1-[5-(1-(3,4-dichlorophenyl)-5-methyl-1H-1,2,4-triazol-3-ylthio)pentyl]piperidine oxalate;
[127] 4-[5-(1-(3,4-dichlorophenyl)-5 ethyl-1H-1,2,4-triazol-ylthio)pentyl]morpholine oxalate;
[128] 1-[5-(1-(3,4-dichlorophenyl)-5-methyl-1H-1,2,4-triazol-3-ylthio)pentyl]pyrrolidine oxalate;
[129] 4-[2-(1-(3,4-dichlorophenyl)-5-methyl-1H-1,2,4-triazol-3-yloxy)ethyl]morpholine oxalate;
[130] 4-[2-(3,4-dichlorophenyl)-5-methyl-1H-1,2,4-triazole-3-ylthio)ethyl]morpholine hydrochloride.
[131] 1-[2-(1-(3,4-dichlorophenyl)-5-methyl-1H-1,2,4-triazol-3-ylthio)ethyl]-4-methyl piperidinium oxalate;
[132] 4-[2-(5-methyl-1-phenyl-1H-1,2,4-triazol-3-ylthio)ethyl]morpholinium oxalate;
[133] 4-[2-(1-(4-chlorophenyl)-5-ethyl-1H-1,2,4-triazol-3-ylthio)ethyl]morpholinium oxalate;
[134] N-[2-(1-(3-chlorophenyl)-5-methyl-1H-1,2,4-triazol-3-ylthio)ethyl]-N,N-diisopropylpropan-2-aminium oxalate
[134] 1-[2-(1-(3-chlorophenyl)-5-methyl-1H-1,2,4-triazol-3-ylthio)ethyl]piperidinium oxalate
[135] 4-[2-(1-chlorophenyl)-5-methyl-1H-1,2,4-triazol-3-ylthio)ethyl]morpholinium oxalate;
[137] 4-[2-(1-(3-chlorophenyl)-5-methyl-1H-1,2,4-triazol-3-ylthio)ethyl]pyrrolidinium oxalate
[138] 2-[1-(3-chlorophenyl)-5-methyl-1H-1,2,4-triazol-3-ylthio]-N,N-diethylethan aminium oxalate.

In a more preferred variant of the invention, the sigma ligand of formula (II) is 4-[2-(3,4-dichlorophenyl)-5-methyl-1H-1,2,4-triazole-3-ylthio ethyl] morpholine oxalate.

The compounds of formula (II) can be prepared as disclosed in the previous application WO2008/055932.

In another preferred embodiment, the sigma ligand in the context of the present invention has the general formula (III) as depicted above.

In another embodiment of the invention, it is preferred that in the compound of formula (III) $R_2$ is preferably hydrogen or alkyl; more preferably hydrogen.

In the compound of formula (III) it is also preferred that m is 1 or 2, and also that n is 0 or 1.

Moreover, in the compound of formula (III) it is also preferred that $R_3$ and $R_4$ are either hydrogen or alkyl; more preferred either hydrogen or methyl; and most preferred both are hydrogen.

Further, it is preferred that in the compound of formula (III) $R_1$ is selected from the group formed by substituted or unsubstituted alkyl, substituted or unsubstituted cycloalkyl, substituted or unsubstituted heterocyclyl and substituted or unsubstituted aryl; more preferred substituted or unsubstituted alkyl, unsubstituted cycloalkyl, unsubstituted aryl and aromatic heterocyclic; and most preferred, methyl, t-butyl, cyclohexyl and phenyl.

Moreover, it is also preferred that $R_5$ and $R_6$ together form a substituted or unsubstituted heterocyclyl having 3 to 7 atoms in the ring, in particular morpholin-4-yl, 2,6-dimethylmorpholin-4-yl, piperidin-1-yl, 4-phenylpiperidin-1-yl, 3-phenylpiperidin-1-yl, 4-benzylpiperazin-1-yl, 4-phenylpiperazin-1-yl, 2-[spiro[isobenzofuran-1(3H), 4'-piperidin]-1'-yl, azepan-1-yl, 1,2,3,4-tetrahydro-isoquinolin-2-yl, pyrrolidin-1-yl, 3-phenyl-pyrrolidin-1-yl, isoindolin-2-yl or imidazol-1-yl; especially when $R_2$ is hydrogen, m is 1 and n is 1; more especially when $R_3$ and $R_4$ are both hydrogen; and even more especially when $R_1$ is substituted or unsubstituted phenyl. Good results are obtained when $R_5$ is benzyl and $R_6$ is methyl.

The above embodiments and preferences for $R_1$ to $R_6$, n, m and the dotted line ----- can be combined to give further preferred compounds.

Particular individual compounds of the invention falling under formula (III) include the compounds listed below:

[139] 4,5,6,7-tetrahydro-4-(2-(morpholin-4-yl)ethyl)-1-phenyl-1H-indazole,
[140] 4,5,6,7-tetrahydro-4-(2-(morpholin-4-yl)ethyl)-1-phenyl-1H-indazole oxalate,
[141] 1-(3,4-dichlorophenyl)-4,5,6,7-tetrahydro-4-(2-(4-phenylpiperidin-1-yl)ethyl)-1H-indazole,
[142] 1-(3,4-dichlorophenyl)-4,5,6,7-tetrahydro-4-(2-(4-phenylpiperidin-1-yl)ethyl)-1H-indazole oxalate,
[143] (E)-4,5,6,7-tetrahydro-4-(2-(morpholin-4-yl)ethylidene)-1-phenyl-1H-indazole,
[144] 1-(3,4-dichlorophenyl)-4,5,6,7-tetrahydro-4-(2-(morpholin-4-yl)ethyl)-1H-indazole,
[145] 1-(3,4-dichlorophenyl)-4,5,6,7-tetrahydro-4-(2-(morpholin-4-yl)ethyl)-1H-indazole oxalate,
[146] 4,5,6,7-tetrahydro-1-phenyl-4-(2-(4-phenylpiperidin-1-yl)ethyl)-1H-indazole,
[147] 4,5,6,7-tetrahydro-1-phenyl-4-(2-(4-phenylpiperidin-1-yl)ethyl)-1H-indazole oxalate,
[148] 4-(2-(4-benzylpiperazin-1-yl)ethyl)-4,5,6,7-tetrahydro-1-phenyl-1H-indazole,
[149] 4,5,6,7-tetrahydro-1-phenyl-4-(2-[spiro[isobenzofuran-1(3H), 4'-piperidin]-1-yl]ethyl)-1H-indazole,
[150] 4,5,6,7-tetrahydro-1-phenyl-4-(2-[sp o[isobenzofuran-1(3H),4'-piperidin]-1-yl]ethyl)-1H-indazole oxalate,
[151] 4,5,6,7-tetrahydro-1-phenyl-4-(2-(piperidin-1-yl)ethyl)-1H-indazole,
[152] 4,5,6,7-tetrahydro-1-phenyl-4-(2-(piperidin-1-yl)ethyl)-1H-indazole oxalate,
[153] (E)-4-(2-(azepan-1-yl)ethylidene)-4,5,6,7-tetrahydro-1-phenyl-1H-indazole,
[154] (E)-4-(2-(azepan-1-yl)ethylidene)-4,5,6,7-tetrahydro-1-phenyl-1H-indazole oxalate,
[155] (E)-4,5,6,7-tetrahydro-1-phenyl-4-(2-(4-phenylpiperidin-1-yl)ethylidene)-1H-indazole,
[156] (E)-4,5,6,7-tetrahydro-1-phenyl-4-(2-[spiro[isobenzofuran-1(3H), 4'-piperidin]-1'-yl]ethylidene)-1H-indazole,
[157] (E)-4,5,6,7-tetrahydro-1-phenyl-4-(2-[spiro[isobenzofuran-1(3H), 4'-piperidin]-1'-yl]ethylidene)-1H-indazole oxalate,
[158] (E)-4,5,6,7-tetrahydro-1-phenyl-4-(2-(4-phenylpiperazin-1-yl)ethylidene)-1H-indazole,
[159] 1,2,3,4-tetrahydro-2-((E)-2-(6,7-dihydro-1-phenyl-1H-indazol-4(5H)-ylidene)ethyl)isoquinoline,
[160] 1,2,3,4-tetrahydro-2-((E)-2-(6,7-dihydro-1-phenyl-1H-indazol-4(5H)-ylidene)ethyl)isoquinoline oxalate,
[161] (E)-4,5,6,7-tetrahydro-1-phenyl-4-(2-(3-phenylpiperidin-1-yl)ethylidene)-1H-indazole,
[162] (E)-4,5,6,7-tetrahydro-1-phenyl-4-(2-(3-phenylpyrrolidin-1-yl)ethylidene)-1H-indazole
[163] (E)-4,5,6,7-tetrahydro-1-phenyl-4-(2-(3-phenylpyrrolidin-1-yl)ethylidene)-1H-indazole oxalate,
[164] (E)-4,5,6,7-tetrahydro-4-(2-(isoindolin-2-yl)ethylidene)-1-phenyl-1H-indazole,
[165] (E)-4,5,6,7-tetrahydro-1-phenyl-4-(2-(piperidin-1-yl)ethylidene)-1H-indazole,
[166] 1-(3,4-dichlorophenyl)-4,5,6,7-tetrahydro-4-(2-(4-phenylpiperazin-1-yl)ethyl)-1H-indazole,
[167] 1-(3,4-dichlorophenyl)-4,5,6,7-tetrahydro-4-(2-(4-phenylpiperazin-1-yl)ethyl)-1H-indazole oxalate,
[168] 1,4,5,6-tetrahydro-4-(2-(morpholin-4-yl)ethyl)-1-phenylcyclopenta[c]pyrazole,
[169] 1,4,5,6-tetrahydro-4-(2-(morpholin-4-yl)ethyl)-1-phenylcyclopenta[c]pyrazole oxalate,
[170] 4,5,6,7-tetrahydro-1-phenyl-4-(2-(4-phenylpiperazin-1-yl)ethyl)-1H-indazole,
[171] 4,5,6,7-tetrahydro-1-phenyl-4-(2-(4-phenylpiperazin-1-yl)ethyl)-1H-indazole oxalate,
[172] 2-(2-(1,4,5,6-tetrahydro-1-phenylcyclopenta[c]pyrazol-4-yl)ethyl)isoindoline,
[173] 2-(2-(1,4,5,6-tetrahydro-1-phenylcyclopenta[c]pyrazol-4-yl)ethyl)isoindoline oxalate,
[174] 1,4,5,6-tetrahydro-1-phenyl-4-(2-(4-phenylpiperidin-1-yl)ethyl)cyclopenta[c]pyrazole,
[175] 1,4,5,6-tetrahydro-1-phenyl-4-(2-(piperidin-1-yl)ethyl)cyclopenta[c]pyrazole,
[176] 1,4,5,6-tetrahydro-1-phenyl-4-(2-(4-phenylpiperazin-1-yl)ethyl)cyclopenta[c]pyrazole,
[177] 1,4,5,6-tetrahydro-1-phenyl-4-(2-(pyrrolidin-1-yl)ethyl)cyclopenta[c]pyrazole,
[178] 1,4,5,6-tetrahydro-1-phenyl-4-(2-(pyrrolidin-1-yl)ethyl)cyclopenta[c]pyrazole oxalate,
[179] 4-(2-(4-benzylpiperazin-1-yl)ethyl)-1,4,5,6-tetrahydro-1-phenylcyclopenta[c]pyrazole,
[180] 4-(2-(4-benzylpiperazin-1-yl)ethyl)-1,4,5,6-tetrahydro-1-phenylcyclopenta[c]pyrazole dioxalate,
[181] 1,2,3,4-tetrahydro-2-(2-(1,4,5,6-tetrahydro-1-phenylcyclopenta[c]pyrazol-4-yl)ethyl)isoquinoline,
[182] 1,2,3,4-tetrahydro-2-(2-(1,4,5,6-tetrahydro-1-phenylcyclopenta[c]pyrazol-4-yl)ethyl)isoquinoline oxalate,
[183] 4-(2-(1H-imidazol-1-yl)ethyl)-1,4,5,6-tetrahydro-1-phenylcyclopenta[c]pyrazole,
[184] cis-1,4,5,6-tetrahydro-4-(2-(2,6-dimethylmorpholin-4-yl)ethyl)-1-phenyl cyclopenta[c]pyrazole,
[185] cis-1,4,5,6-tetrahydro-4-(2-(2,6-dimethylmorpholin-4-yl)ethyl)-1-phenyl cyclopenta[c]pyrazole oxalate,
[186] cis-4,5,6,7-tetrahydro-4-(2-(2,6-dimethylmorpholin-4-yl)ethyl)-1-phenyl-1H-indazole,
[187] cis-4,5,6,7-tetrahydro-4-(2-(2,6-dimethylmorpholin-4-yl)ethyl)-1-phenyl-1H-indazole oxalate,
[188] 1,4,5,6-tetrahydro-1-phenyl-4-(2-[spiro[isobenzofuran-1(3H), 4'-piperidin]-1'-yl]-ethyl)cyclopenta[c]pyrazole,
[189] 1,4,5,6-tetrahydro-1-phenyl-4-(2-[spiro[isobenzofuran-1(3H), 4'-piperidin]-1'-yl]-ethyl)cyclopenta[c]pyrazole oxalate,
[190] N-benzyl-2-(1,4,5,6-tetrahydro-1-phenylcyclopenta[c]pyrazol-4-yl)-N-methyl-ethanamine,
[191] diastereomeric mixture of 1,4,5,6-tetrahydro-1-phenyl-4-(2-(3-phenylpiperidin-1-yl)ethyl)cyclopenta[c]pyrazole,
[192] N-benzyl-2-(4,5,6,7-tetrahydro-1-phenyl-1H-indazol-4-yl)-N-methylethanamine,
[193] 4,5,6,7-tetrahydro-4-(2-(isoindolin-2-yl)ethyl)-1-phenyl-1H-indazole,
[194] 4,5,6,7-tetrahydro-4-(2-(isoindolin-2-yl)ethyl)-1-phenyl-1H-indazole oxalate,
[195] 4,5,6,7-tetrahydro-1-methyl-4-(2-(4-phenylpiperidin-1-yl)ethyl)-1H-indazole,
[196] 4,5,6,7-tetrahydro-1-methyl-4-(2-(4-phenylpiperidin-1-yl)ethyl)-1H-indazole oxalate,
[197] 4,5,6,7-tetrahydro-4-(2-(isoindolin-2-yl)ethyl)-1-methyl-1H-indazole,
[198] 4,5,6,7-tetrahydro-4-(2-(isoindolin-2-yl)ethyl)-1-methyl-1H-indazole oxalate,
[199] N-benzyl-2-(4,5,6,7-tetrahydro-1-methyl-1H-indazol-4-yl)-N-methylethanamine,
[200] N-benzyl-2-(4,5,6,7-tetrahydro-1-methyl-1H-indazol-4-yl)-N-methylethanamine oxalate,
[201] 4,5,6,7-tetrahydro-1-methyl-4-(2-(morpholin-4-yl)ethyl)-1H-indazole,

[202] 4,5,6,7-tetrahydro-1-methyl-4-(2-(morpholin-4-yl)ethyl)-1H-indazole oxalate,
[203] 1-(4-fluorophenyl)-4,5,6,7-tetrahydro-4-(2-(morpholin-4-yl)ethyl)-1H-indazole,
[204] 1-(4-fluorophenyl)-4,5,6,7-tetrahydro-4-(2-(morpholin-4-yl)ethyl)-1H-indazole oxalate,
[205] cis-1-(4-fluorophenyl)-4,5,6,7-tetrahydro-4-(2-(2,6-dimethylmorpholin-4-yl)ethyl)-1H-indazole,
[206] cis-1-(4-fluorophenyl)-4,5,6,7-tetrahydro-4-(2-(2,6-dimethylmorpholin-4-yl)ethyl)-1H-indazole oxalate,
[207] N-benzyl-2-(1-(4-fluorophenyl)-4,5,6,7-tetrahydro-1H-indazol-4-yl)-N-methyl-ethanamine,
[208] 1-(4-fluorophenyl)-4,5,6,7-tetrahydro-4-(2-(isoindolin-2-yl)ethyl)-1H-indazole,
[209] 1-(4-fluorophenyl)-4,5,6,7-tetrahydro-4-(2-(isoindolin-2-yl)ethyl)-1H-indazole oxalate,
[210] 1-(4-fluorophenyl)-4,5,6,7-tetrahydro-4-(2-(4-phenylpiperidin-1-yl)ethyl)-1H-indazole,
[211] (+)-4,5,6,7-tetrahydro-4-(2-(morpholin-4-yl)ethyl)-1-phenyl-1H-indazole,
[222] (+)-4,5,6,7-tetrahydro-4-(2-(morpholin-4-yl)ethyl)-1-phenyl-1H-indazole oxalate,
[223] (−)-4,5,6,7-tetrahydro-4-(2-(morpholin-4-yl)ethyl)-1-phenyl-1H-indazole,
[224] (+4,5,6,7-tetrahydro-4-(2-(morpholin-4-yl)ethyl)-1-phenyl-1H-indazole oxalate,
[215] (E)-4,5,6,7-tetrahydro-4-(2-(morpholin-4-yl)ethylidene)-1-phenyl-1H-indazole oxalate,
[216] (E)-4,5,6,7-tetrahydro-1-phenyl-4-(2-(piperidin-1-yl)ethyliden-1H-indazole oxalate,
[217] (E)-N-benzyl-2-(6,7-dihydro-1-phenyl-1H-indazol-4(5H)-ylidene)-N-methyl-ethanamine,
[218] (E)-N-benzyl-2-(6,7-dihydro-1-phenyl-1H-indazol-4(5H)-ylidene)-N-methyl-ethanamine oxalate,
[219] (E)-4,5,6,7-tetrahydro-4-(2-(cis-2,6-dimethylmorpholin-4-yl)ethylidene)-1-phenyl-1H-indazole,
[220] (E)-4,5,6,7-tetrahydro-4-(2-(cis-2,6-dimethylmorpholin-4-yl)ethylidene)-1-phenyl-1H-indazole oxalate,
[221] (E)-1-(3,4-dichlorophenyl)-4,5,6,7-tetrahydro-4-(2-(cis-2,6-dimethylmorpholino-4-yl)-ethylidene)-1H-indazole,
[222] (E)-1-(3,4-dichlorophenyl)-4,5,6,7-tetrahydro-4-(2-(cis-2,6-dimethyl-morpholino-4-yl)ethylidene)-1H-indazole oxalate,
[223] (E)-1-(3,4-dichlorophenyl)-4,5,6,7-tetrahydro-4-(2-(morpholino-4-yl)ethylidene)-1H-indazole,
[224] (E)-1-(3,4-dichlorophenyl)-4,5,6,7-tetrahydro-4-(2-(morpholino-4-yl)-ethylidene)-1H-indazole oxalate,
[225] (E)-1-(3,4-dichlorophenyl)-4,5,6,7-tetrahydro-4-(2-(piperidin-1-yl)ethylidene)-1H-indazole,
[226] (E)-1-(3,4-dichlorophenyl)-4,5,6,7-tetrahydro-4-(2-(piperidin-1-yl)-ethylidene)-1H-indazole oxalate,
[227] (E)-4-(2-(N,N-diethylamino)ethylidene)-4,5,6,7-tetrahydro-1-phenyl-1H-indazole,
[228] (E)-4-(2-(N,N-diethylamino)ethylidene)-4,5,6,7-tetrahydro-1-phenyl-1H-indazole oxalate,
[229] (E)-4-(2-(4-cyclohexylpiperazin-1-yl)ethylidene)-4,5,6,7-tetrahydro-1-phenyl-1H-indazole,
[230] (E)-4,5,6,7-tetrahydro-4-(2-(4-methylpiperidin-1-yl)ethylidene)-1-phenyl-1H-indazole,
[231] 4,5,6,7-tetrahydro-4-(2-(4-methylpiperidin-1-yl)ethyl)-1-phenyl-1H-indazole,
[232] 4,5,6,7-tetrahydro-4-(2-(4-methylpiperidin-1-yl)ethyl)-1-phenyl-1H-indazole oxalate,
[233] 1,4,5,6-tetrahydro-1-phenyl-4-(2-(piperidin-1-yl)ethyl)cyclopenta[c]pyrazole oxalate,
[234] 1,4,5,6-tetrahydro-1-phenyl-4-[2-(thiomorpholin-4-yl)ethyl]cyclopenta[c]pyrazole,
[235] 1,4,5,6-tetrahydro-1-phenyl-4-[2-(thiomorpholin-4-yl)ethyl]cyclopenta[c]pyrazole oxalate,
[236] 1,4,5,6-tetrahydro-4-(2-(4-methylpiperidin-1-yl)ethyl)-1-phenylcyclopenta[c]pyrazole,
[237] 1,4,5,6-tetrahydro-4-(2-(4-methylpiperidin-1-yl)ethyl)-1-phenylcyclopenta[c]pyrazole oxalate,
[238] 1,4,5,6-tetrahydro-4-(2-(4-methylpiperazin-1-yl)ethyl)-1-phenylcyclopenta[c]pyrazole,
[239] 4-(2-(4-cyclohexylpiperazin-1-yl)ethyl)-1,4,5,6-tetrahydro-1-phenylcyclopenta[c]pyrazole,
[240] 4-(2-(azepan-1-yl)ethyl)-4,5,6,7-tetrahydro-1-phenyl-1H-indazole,
[241] N-benzyl-2-(1-tert-butyl-4,5,6,7-tetrahydro-1H-indazol-4-yl)-N-methylethan amine,
[242] 1-tert-butyl-4,5,6,7-tetrahydro-4-(2-(4-phenylpiperidin-1-yl)ethyl)-1H-indazole,
[243] 1-tert-butyl-4,5,6,7-tetrahydro-4-(2-(4-phenylpiperidin-1-yl)ethyl)-1H-indazole oxalate,
[244] (−)-N-bencyl-2-(4,5,6,7-tetrahydro-1-methyl-1H-indazol-4-yl)-N-methylethan amine,
[245] (+)-N-bencyl-2-(4,5,6,7-tetrahydro-1-methyl-1H-indazol-4-yl)-N-methylethan amine,
[246] N-(2-(4,5,6,7-tetrahydro-1-methyl-1H-indazol-4-yl)ethyl)-N-methylcyclohexanamine,
[247] 4,5,6,7-tetrahydro-4-(2-(4-hydroxy-4-phenylpiperidin-1-yl)ethyl)-1-methyl-1H-indazole,
[248] 4,5,6,7-tetrahydro-1-methyl-4-(2-(4-phenylpiperidin-1-yl)ethyl)-1H-indazole.
[249] N-benzyl-2-(4,5,6,7-tetrahydro-1-methyl-1H-indazol-4-yl)-N-methylethanamine,
[250] 4,5,6,7-tetrahydro-1-phenyl-4-(2-[spiro[isobenzofuran-1(3H), 4'-piperidin]-1-yl]-ethyl)-1H-indazole.

Although the oxalates are listed, other pharmaceutically acceptable salts also form part of this group of preferred compounds.

In a more preferred variant of the invention, the sigma ligand of formula (III) are selected from:

[251] 4-(2-(1-(4-fluorophenyl)-4,5,6,7-tetrahydro-1H-indazol-4-yl)ethyl)morpholine oxalate;
[252] 4-(1-(2-(1-methyl)-4,5,6,7-tetrahydro-1H-indazol-4-yl)ethyl)piperidin-4-yl)benzonitrile oxalate; and
[253] 1-(4-(7-((5-bromothiophen-2-yl)methyl)-5,6,7,8-tetrahydropyrido[3,4-d]pyrimidin-2-ylamino)phenyl)ethyl acetate.

The compounds of formula (III) can be prepared as disclosed in the previous application WO2006/021463.

In a particular embodiment of the present invention, the pain developed as a consequence of surgery is superficial and/or deep pain and for example is peripheral neuropathic pain, with neuralgia, allodynia, causalgia, hyperalgesia, hyperesthesia and/or hyperpathia.

In another aspect of the present invention, the pain developed as a consequence of surgery as defined herein before is accompanied by neuropathy and/or neuritis. More preferably, the pain is thermal hyperalgesia or mechanical allodynia.

"Neuropathic pain" is defined by the IASP as "pain initiated or caused by a primary lesion or dysfunction in the nervous system" (IASP, Classification of chronic pain, $2^{nd}$ Edition, IASP Press (2002), 210). For the purpose of this invention this term is to be treated as synonymous to "Neurogenic Pain" which is defined by the IASP as "pain initiated or caused by a primary lesion, dysfunction or transitory perturbation in the peripheral or central nervous system". Neuropathic pain according to this invention is restricted to the neuropathic pain resulting from a surgery.

According to the IASP "allodynia" is defined as "a pain due to a stimulus which does not normally provoke pain" (IASP, Classification of chronic pain, $2^{nd}$ Edition, ASP Press (2002), 210). According to the IASP "peripheral neuropathic pain" is defined as "a pain initiated or caused by a primary lesion or dysfunction in the peripheral nervous system" and "peripheral neurogenic pain" is defined as "a pain initiated or caused by a primary lesion, dysfunction or transitory perturbation in the peripheral nervous system" (IASP, Classification of chronic pain, $2^{nd}$ Edition, IASP Press (2002), 213).

According to the IASP "causalgia" is defined as "a syndrome of sustained burning pain, allodynia and hyperpathia after a traumatic nerve lesion, often combined with vasomotor and sudomotor dysfunction and later trophic changes" (IASP, Classification of chronic pain, $2^{nd}$ Edition, IASP Press (2002), 210).

According to the IASP "hyperalgesia" is defined as "an increased response to a stimulus which is normally painful" (IASP, Classification of chronic pain, $2^{nd}$ Edition, IASP Press (2002), 211).

According to the IASP "hyperesthesia" is defined as "increased sensitivity to stimulation, excluding the senses" (IASP, Classification of chronic pain, $2^{nd}$ Edition, IASP Press (2002), 211).

According to the IASP "hyperpathia" is defined as "a painful syndrome characterized by an abnormally painful reaction to a stimulus, especially a repetitive stimulus, as well as an increased threshold" (IASP, Classification of chronic pain, $2^{nd}$ Edition, IASP Press (2002), 212).

The IASP draws the following difference between "allodynia", "hyperalgesia" and "hyperpathia" (IASP, Classification of chronic pain, $2^{nd}$ Edition, ASP Press (2002), 212):

| Allodynia | Lowered threshold | Stimulus and response mode differ |
| Hyperalgesia | Increased response | Stimulus and response rate are the same |
| Hyperpathia | Raised threshold Increased response | Stimulus and response rate may be the same or different |

According to the IASP "neuralgia" is defined as "pain in the distribution of a nerve or nerves" (IASP, Classification of chronic pain, $2^{nd}$ Edition, IASP Press (2002), 212).

According to the IASP "neuritis" is defined as "inflammation of a nerve or nerves" (IASP, Classification of chronic pain, $2^{nd}$ Edition, IASP Press (2002), 212).

According to the IASP "neuropathy/neuritis" is defined as "a disturbance of function or pathological change in a nerve: in one nerve mononeuropathy, in several nerves mononeuropthy multiplex, if diffuse and bilateral, polyneuropathy" (IASP, Classification of chronic pain, $2^{nd}$ Edition, IASP Press (2002), 212).

As stated previously, one aspect of this invention refers to the use of sigma ligand as defined above for the manufacture of a medicament for the prevention and/or treatment of the pain developed as a consequence to surgery.

The auxiliary materials or additives of a pharmaceutical composition according to the present invention can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition comprising the sigma ligand in accordance with the invention can be adapted to any form of administration, be it orally or parenterally, for example pulmonar, nasally, rectally and/or intravenously. Therefore, the formulation in accordance with the invention may be adapted for topical or systemic application, particularly for dermal, transdermal, subcutaneous, intramuscular, intra-articular, intraperitoneal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intracisternal, intraspinal, perispinal, intracranial, delivery via needles or catheters with or without pump devices, or other application routes.

Suitable preparations for oral applications are tablets, pills, caplets, gel caps, chewing gums, capsules, granules, drops or syrups.

Suitable preparations for parenteral applications are solutions, suspensions, reconstitutable dry preparations, aerosols or sprays.

The composition of the invention may be formulated as deposits in dissolved form or in patches, for percutaneous application.

Skin applications include ointments, gels, creams, lotions, suspensions or emulsions.

Suitable form of rectal application is by means of suppositories.

Moreover, the composition may be presented in a form suitable for once daily, weekly, or monthly administration.

Accordingly, in another aspect the invention provides a method of treatment of a patient suffering from post-surgical pain, or likely to suffer pain as a result of a surgical operation, which comprises administering to the patient in need of such a treatment or prophylaxis a therapeutically effective amount of a sigma ligand at the appropriate treatment frequency as defined above.

In some embodiments, the post-surgical pain includes one or more of: allodynia, hyperalgesia, thermally induced pain, mechanically induced pain, or resting pain. For instance, post-surgical pain can include mechanically induced pain and/or resting pain. In some cases, the post-surgical pain includes resting pain.

In certain embodiments, allodynia is suppressed, ameliorated and/or prevented, and in some embodiments, hyperalgesia is suppressed, ameliorated and/or prevented. In some instances, the pain is chronic pain. In other cases, the pain is at, proximal and/or near to one or more site(s) of external trauma, wound or incision. Additional aspects of the subject methods include methods of ameliorating and/or preventing the development or progression of post-surgical pain by administering the subject sigma ligands. In certain embodiments, the sigma ligand can be administered prior to an activity likely to result in external trauma, wound or incision, such as surgery. For example, the emulsion formulation can be administered 30 minutes, 1 hour, 2 hours, 5 hours, 10 hours, 15 hours, 24 hours or even more, such as 1 day, several days, or even a week, two weeks, three weeks, or more prior to the activity likely to result in external trauma, wound or incision, such as prior to surgery. In other embodiments, the sigma ligand can be administered during and/or after surgery or activity that resulted in external trauma, wound or incision. In some instances, the sigma ligand is administered 1 hour, 2 hours, 3 hours, 4 hours, 6 hours, 8 hours, 12 hours, 24 hours, 30 hours, 36 hours, or more, after surgery, or activity that resulted in external trauma, wound or incision.

In one embodiment of the invention it is preferred that the sigma ligand is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of pain being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

For example, the dosage regime that must be administered to the patient will depend on the patient's weight, the type of application, the condition and severity of the disease. A preferred dosage regime of comprises an administration of a compound according the present invention within a range of 0.01 to 300 mg/kg, more preferably 0.01 to 100 mg/kg, and most preferable 0.01 to 50 mg/kg.

The following examples are merely illustrative of certain embodiments of the invention and cannot be considered as restricting it in any way.

EXAMPLES

Example 1. Synthesis of 4-{2-[5-Methyl-1-(naphthalen-2-yl)-1H-pyrazol-3-yloxy]ethyl}morpholine (compound 63) and its hydrochloride salt

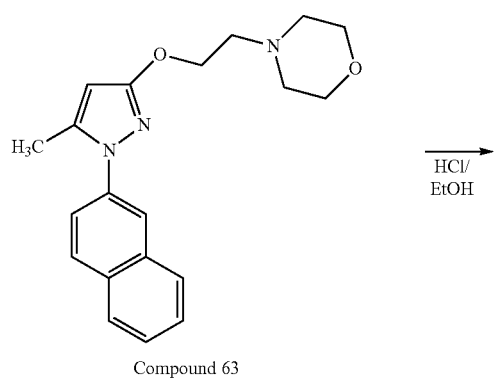

Compound 63

-continued

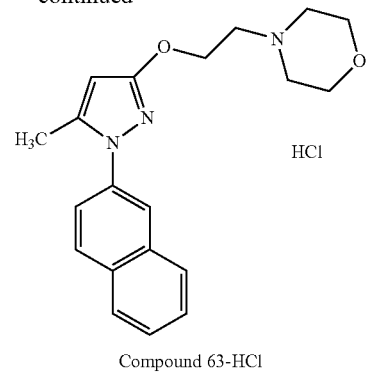

Compound 63-HCl

Compound 63 can be can be prepared as disclosed in the previous application WO2006/021462. Its hydrochloride can be obtained according the following procedure:

Compound 63 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.)

$^1$H-NMR (DMSO-$d_5$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%

Example 2. Assessment of Analgesic Activity Against Post-Operative Pain in Rats

The induction of anaesthesia in rats was performed with 3% isofluran for veterinary use, employing an Ohmeda vaporizer and an anaesthesia chamber. Anaesthesia was kept during the surgical operation by a tube which directs the isofluran vapours to the animal's snout. Once the rats were anaesthetised, they were laid down in a prone position and their right hindpaws were cleaned out with alcohol.

Then, a skin incision in the hindpaw of about 10 mm was made by means of a scalpel, starting about 5 mm from the heel and extending toward the toes. Fascia was located and by means of curve scissors muscle was elevated and a longitudal incision of about 5 mm was made, thus the muscle origin and insertion remained intact. Therefore, both superficial (skin) and deep (muscle) tissues and nerves were injured. The skin of the paw was stitched with a suturing stitch with breaded silk (3.0) and the wound was cleaned out with povidone.

The assessment was performed always 4 hours after the surgery (plantar incision), 30 or 60 minutes after the administration of said product. Two types of analysis were carried out:

Mechanical allodynia was tested using von Frey filaments: Animals were placed in methacrylate cylinders on an elevated surface, with metallic mesh floor perforated in order to apply the filaments. After an acclimation period of about 30 minutes within the cylinders, both hindpaws were stimulated (the injured and the non-injured paw, serving the latter as control), starting with the lowest force filament (0.4 g) and reaching a 15 g filament. The animal's response to pain was manifested by the withdrawal of the paw as a consequence of the painful stimulus caused by a filament. The pressure (force in grams) threshold eliciting the withdrawal of the paw was recorded.

The thermal hyperalgesia was tested using a Ugo Basile plantar test: Animals were placed in the methacrylate cages of said apparatus, having a crystal floor. The acclimatation period within the cages was about 10 minutes. The thermal stimulus came from a lamp moving below the crystal floor and which was applied to both paws, with a minimum interval of 1 minute between both stimulations in order to avoid learning behaviours. The rat was able to withdraw the paw freely when it feels the pain produced by the heat coming from the lamp; then it is switched off and the latency time to the withdrawal response is recorded in seconds. In order to avoid hurting the animal's paw, the lamp was automatically switched off after 32 seconds.

Plantar Inicision—Mechanical Allodynia

Figure 1:
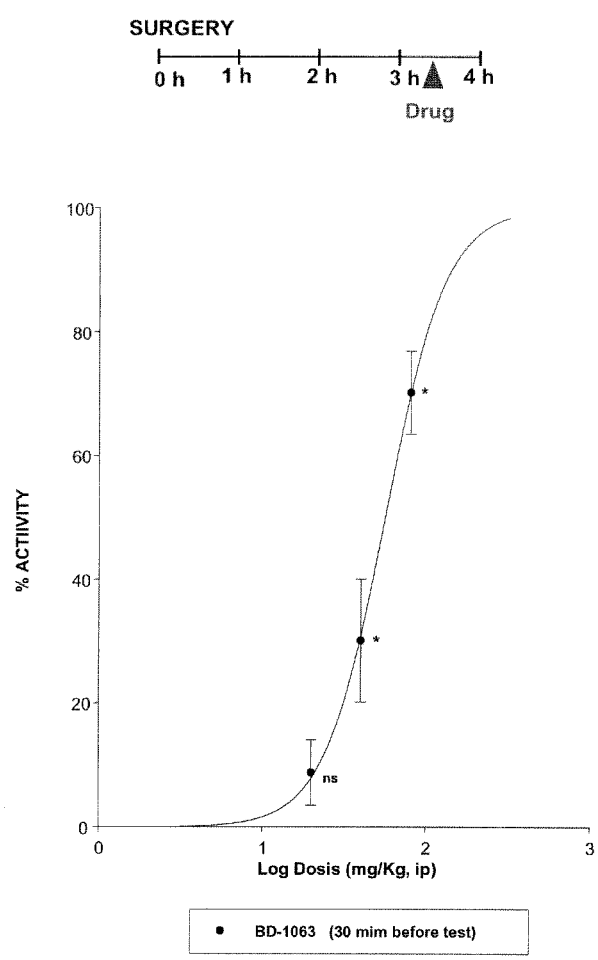
FIG. 1: Treatment approach in mechanical allodynia. Results obtained with a known Sigma ligand (BD-1063) administered intraperitoneally 30 min before mechanical allodynia was assessed in the ipsilateral (operated) hindpaw of rats [0 h: surgery; 3.5 h: administration i.p. of the compound; 4 h: mechanical allodynia assessment; *: significant differences (p<0.05); ns: non-significant differences (p>0.05); n=10].

Treatment:

FIG. 1: Results obtained with a known Sigma ligand (BD-1063) administered intraperitoneally 30 min before mechanical allodynia was assessed in the ipsilateral (operated) hindpaw of rats.

Figure 2:
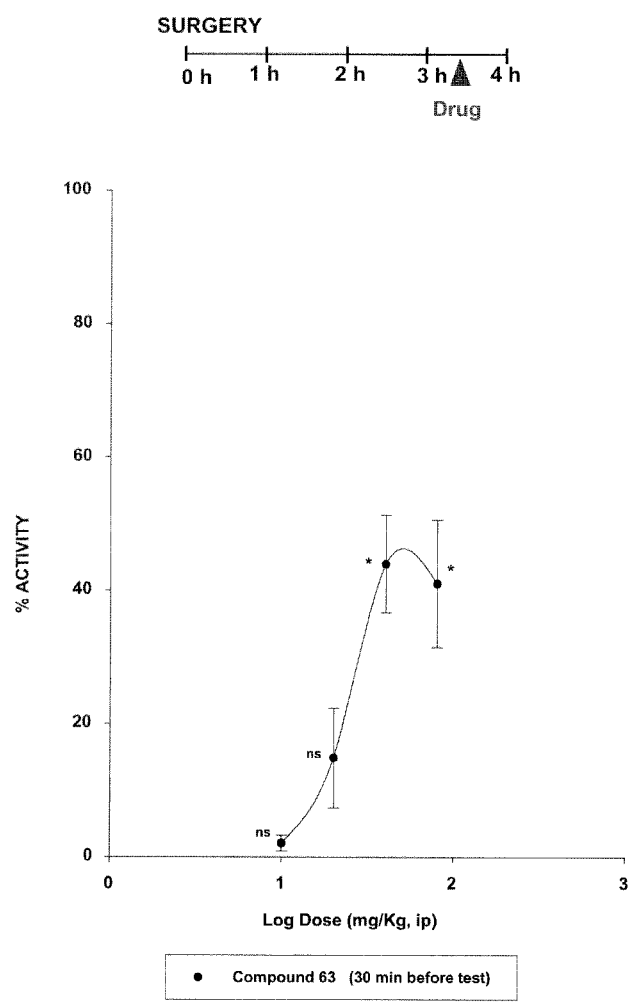
FIG. 2: Treatment approach in mechanical allodynia. Results obtained with compound 63 administered intraperitoneally 30 min before mechanical allodynia was assessed in the ipsilateral (operated) hindpaw of rats [0 h: surgery; 3.5 h: administration i.p. of the compound; 4 h: mechanical allodynia assessment; *: significant differences (p<0.05); ns: non-significant differences (p>0.05); n=10].

FIG. 2: Results obtained with compound 63 administered intraperitoneally 30 min before mechanical allodynia was assessed in the ipsilateral (operated) hindpaw of rats.

Prevention/Treatment Comparison:

FIG. 3: Comparative results of mechanical allodynia obtained with sodium diclofenac, commonly used for the post-surgical pain treatment, administered before (prevention) and after (treatment) surgery in the ipsilateral (operated) hindpaw of rats.

FIG. 4: Comparative results of mechanical allodynia for BD-1063 and compound 63 administered before (prevention) and after (treatment) surgery in the ipsilateral (operated) hindpaw of rats.

Plantar Inicision—Thermal Hyperalgesia

Prevention/Treatment Comparison:

FIG. 5: Comparative results of thermal hyperalgesia obtained with sodium diclofenac, commonly used for the post-surgical pain treatment, administered before (prevention) and after (treatment) surgery in the ipsilateral (operated) hindpaw of rats.

FIG. 6: Comparative results of thermal hyperalgesia for compound 63 administered before (prevention) and after (treatment) surgery in the ipsilateral (operated) hindpaw of rats.

The main issue observed in thermal hyperalgesia is the same as for the previous test described (mechanical allodynia).

Sigma ligands are effective against post-operative pain by reducing both mechanical allodynia and thermal hyperalgesia. It is important to note that activity is seen both when administered before (prevention) and after (treatment) surgery and that, in contrast to diclofenac (FIGS. 3 and 5), the potency increases when the compound was administered before the surgery (FIGS. 4 and 6).

The invention claimed is:

1. A method of treatment of postoperative pain developed as a consequence of surgery of a patient, which comprises administering to the patient an amount of a sigma ligand effective alone to treat postoperative pain developed as, a consequence of surgery of the patient, wherein the sigma ligand is 4-{2-[5-methyl-1-(naphthalen-2-yl)-1H-pyrazol-3-yloxy]ethyl} morpholine or a pharmaceutically acceptable salt, isomer or solvate thereof.

2. The method according to claim 1, wherein the pain is acute or chronic postoperative pain developed as a consequence of surgery.

3. The method according to claim 1, wherein the sigma ligand is 4-{2-[5-methyl-1-(naphthalen-2-yl)-1H-pyrazol-3-yloxy]ethyl} morpholine hydrochloride.

4. The method according to claim 2, wherein the postoperative pain developed as a consequence of surgery is allodynia developed as a consequence of surgery, or hyperalgesia developed as a consequence of surgery.

5. The method according to claim 1, wherein the amount of the sigma ligand is administered prior to surgery.

6. The method according to claim 5, wherein the amount of the sigma ligand is administered 30 minutes, 1 hour, 2 hours, 5 hours, 10 hours, 15 hours, 24 hours, or more, prior to surgery.

7. The method according to claim 1, wherein the amount of the sigma ligand is administered during surgery.

8. The method according to claim 1, wherein the amount of the sigma ligand is administered after surgery.

9. The method according to claim 1, wherein the amount of the sigma ligand is administered during and after surgery.

10. The method according to claim 8 or 9, wherein the amount of the sigma ligand is administered 1 hour, 2 hours, 3 hours, 4 hours, 6 hours, 8 hours, 12 hours, 24 hours, 30 hours, 36 hours, or more, after surgery.

* * * * *